(12) United States Patent
Liu et al.

(10) Patent No.: US 11,721,838 B2
(45) Date of Patent: Aug. 8, 2023

(54) ELECTROLYTE AND ELECTROCHEMICAL APPARATUS

(71) Applicant: Ningde Amperex Technology Limited, Ningde (CN)

(72) Inventors: Jian Liu, Ningde (CN); Wenqiang Li, Ningde (CN); Jianming Zheng, Ningde (CN); Xiexue Peng, Ningde (CN)

(73) Assignee: NINGDE AMPEREX TECHNOLOGY LIMITED, Ningde (CN)

( * ) Notice: Subject to any disclaimer, the term of this patent is extended or adjusted under 35 U.S.C. 154(b) by 128 days.

(21) Appl. No.: 17/217,211

(22) Filed: Mar. 30, 2021

(65) Prior Publication Data

US 2021/0408597 A1 Dec. 30, 2021

(30) Foreign Application Priority Data

Jun. 24, 2020 (CN) .......................... 202010589207.2

(51) Int. Cl.
*H01M 10/0567* (2010.01)
*H01M 10/0569* (2010.01)
(Continued)

(52) U.S. Cl.
CPC ....... *H01M 10/0567* (2013.01); *C07C 255/03* (2013.01); *C07C 255/04* (2013.01);
(Continued)

(58) Field of Classification Search
None
See application file for complete search history.

(56) References Cited

U.S. PATENT DOCUMENTS 9,343,776 B2 5/2016 Chang et al.
10,141,601 B2 11/2018 Chang et al.
(Continued)

FOREIGN PATENT DOCUMENTS

CN 102629696 A 8/2012
CN 106104869 A 11/2016
(Continued)

OTHER PUBLICATIONS

Office Action dated Mar. 22, 2021, issued in counterpart CN application No. 202010589207.2 (14 pages).
(Continued)

*Primary Examiner* — Christopher P Domone
(74) *Attorney, Agent, or Firm* — WHDA, LLP

(57) ABSTRACT

An electrolyte including an additive of compound of formula I,

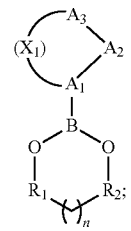

formula I wherein n is an integer ranging from 0 to 10;
$R_1$ and $R_2$ are each independently selected from a substituted or unsubstituted $C_1$-$C_{10}$ alkylidene group, a substituted or unsubstituted $C_2$-$C_{10}$ alkenylene group, or a substituted or unsubstituted $C_1$-$C_{10}$ alkyleneoxy group;
$A_1$ selected from CH, C, N, S, O, B or Si; $A_2$ is selected
(Continued)

from CH—$R_3$, N—$R_3$, S, O, B—$R_3$ or SiH—$R_3$; $A_3$ selected from $CH_2$, CH, C, N, S, O, B or Si; $R_3$ is selected from hydrogen, halogen, a substituted or unsubstituted $C_1$-$C_{10}$ alkyl group, or a substituted or unsubstituted $C_3$-$C_{10}$ cycloalkyl group; $X_1$ is selected from a substituted or unsubstituted $C_1$-$C_{10}$ alkylidene group, a substituted or unsubstituted $C_2$-$C_{10}$ alkenylene group, =$R^e$=, or =$R^e$—, wherein $R^e$ is selected from a substituted or unsubstituted $C_2$-$C_6$ alkylidene group.

13 Claims, 1 Drawing Sheet

(51) Int. Cl.
| | | |
|---|---|---|
| *H01M 10/0568* | (2010.01) | |
| *H01M 10/0525* | (2010.01) | |
| *H01M 4/525* | (2010.01) | |
| *C07F 5/02* | (2006.01) | |
| *C07C 261/02* | (2006.01) | |
| *C07C 255/04* | (2006.01) | |
| *C07C 255/03* | (2006.01) | |
| *C07C 255/05* | (2006.01) | |
| *C07C 317/28* | (2006.01) | |
| *H01M 4/02* | (2006.01) | |

(52) U.S. Cl.
CPC .......... *C07C 255/05* (2013.01); *C07C 261/02* (2013.01); *C07C 317/28* (2013.01); *C07F 5/027* (2013.01); *H01M 4/525* (2013.01); *H01M 10/0525* (2013.01); *H01M 10/0568* (2013.01); *H01M 10/0569* (2013.01); *H01M 2004/028* (2013.01); *H01M 2300/004* (2013.01)

(56) References Cited

U.S. PATENT DOCUMENTS

| | | | | |
|---|---|---|---|---|
| 2016/0118686 | A1* | 4/2016 | Kim | H01M 10/0567 429/188 |
| 2016/0181609 | A1* | 6/2016 | Shin | C01G 51/006 252/182.1 |
| 2017/0018772 | A1 | 1/2017 | Satow et al. | |
| 2020/0052322 | A1* | 2/2020 | Yu | H01M 10/052 |
| 2020/0161702 | A1 | 5/2020 | Ma et al. | |
| 2020/0388885 | A1* | 12/2020 | Ji | H01M 4/808 |

FOREIGN PATENT DOCUMENTS

| | | |
|---|---|---|
| CN | 106532120 A | 3/2017 |
| CN | 108417894 A | 8/2018 |
| CN | 109361018 A | 2/2019 |
| CN | 109786824 A | 5/2019 |
| CN | 110010955 A | 7/2019 |
| CN | 110112465 A | 8/2019 |
| CN | 110176630 A | 8/2019 |
| CN | 110783626 A | 2/2020 |
| CN | 111261939 A | 6/2020 |
| JP | 2001143703 A | 5/2001 |
| JP | 2020-77542 A | 5/2020 |
| WO | 2020/151647 A1 | 7/2020 |

OTHER PUBLICATIONS

Office Action dated Jun. 7, 2021, issued in counterpart CN Application No. 202010589207.2. (10 pages).

* cited by examiner

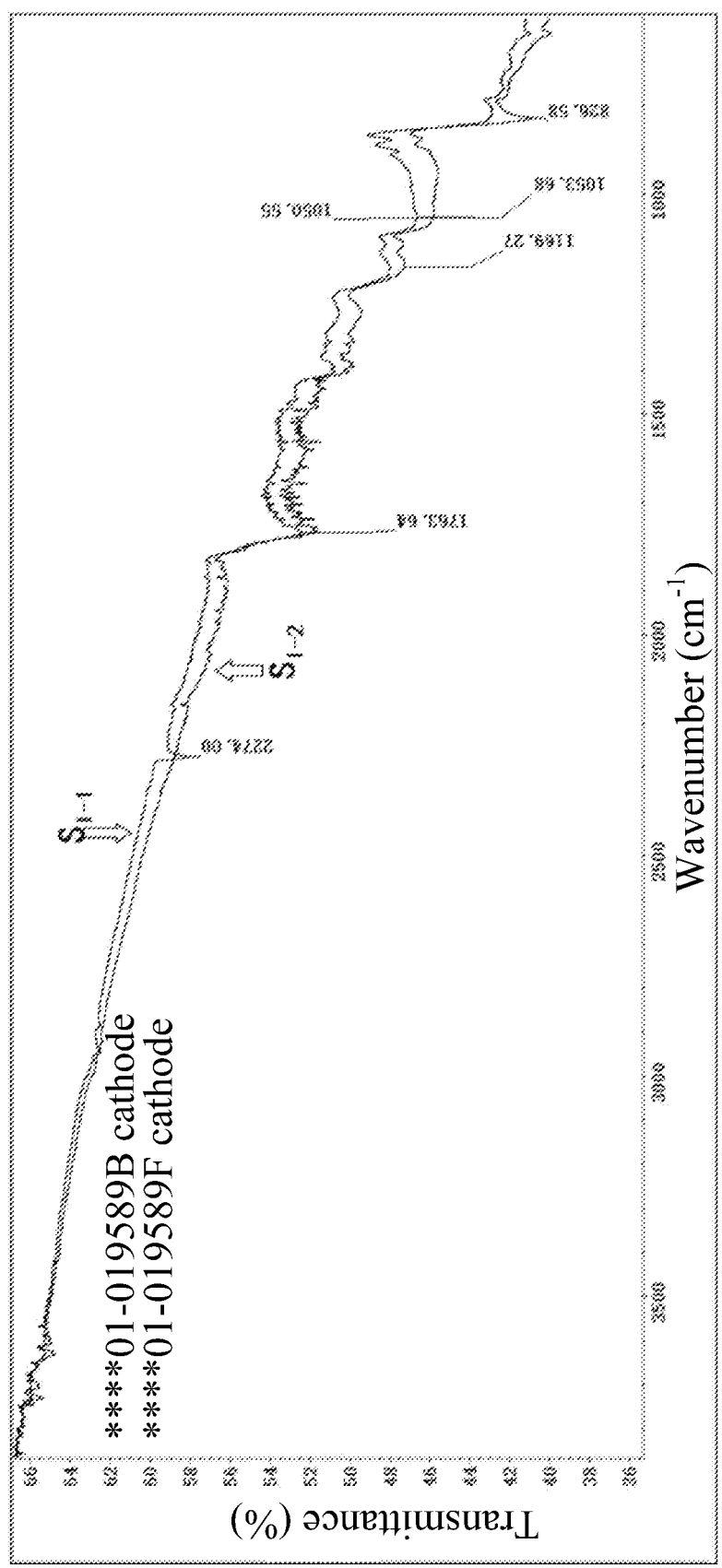

ELECTROLYTE AND ELECTROCHEMICAL APPARATUS

CROSS REFERENCE TO RELATED APPLICATIONS

The present application claims the benefit of priority from the Chinese Patent Application No. 202010589207.2, filed on 24 Jun. 2020, the disclosure of which is hereby incorporated by reference in its entirety.

TECHNICAL FIELD

This application relates to the field of energy storage technologies, and in particular, to an electrolyte and an electrochemical apparatus containing the electrolyte.

BACKGROUND

Lithium-ion batteries have advantages such as environmental friendliness, high energy density, high working voltage and long cycle life, and have been widely used in the fields of electric vehicles, consumer electronics and energy storage apparatuses. With the advantages of high energy density and no memory effect, the lithium-ion battery has gradually become the mainstream battery in these fields. With the continuous development of science and technology, requirements for energy density and working voltage of an electrochemical apparatus are getting higher and higher, and thus how to further improve the above performance has become an urgent problem in the industry.

SUMMARY

This application provides an electrolyte and an electrochemical apparatus containing the electrolyte. The electrolyte according to this application could improve service life and oxidation resistance of an electrochemical apparatus, reduce by-products produced by decomposition of the electrolyte, and inhibit thickness expansion of a battery during a cycle. The electrolyte is applicable to electrochemical apparatuses with high voltage and high energy density, and has a broad application prospect.

In one aspect, this application provides an electrolyte. In some embodiments, the electrolyte includes a compound of formula I:

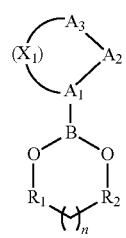

formula I where n is an integer ranging from 0 to 10;

$R_1$ and $R_2$ are each independently selected from a substituted or unsubstituted $C_1$-$C_{10}$ alkylidene group, a substituted or unsubstituted $C_2$-$C_{10}$ alkenylene group, or a substituted or unsubstituted $C_1$-$C_{10}$ alkyleneoxy group, where when substituted, the substituent is one or more selected from the group consisting of a $C_1$-$C_6$ alkyl group, a $C_2$-$C_6$ alkenyl group, a $C_1$-$C_6$ alkoxy group, halogen and a cyano group;

$A_1$ selected from CH, C, N, S, O, B or Si;

$A_2$ is selected from CH—$R_3$, N—$R_3$, S, O, B—$R_3$ or SiH—$R_3$;

$A_3$ selected from $CH_2$, CH, C, N, S, O, B or Si;

$R_3$ is selected from hydrogen, halogen, a substituted or unsubstituted $C_1$-$C_{10}$ alkyl group, or a substituted or unsubstituted $C_3$-$C_{10}$ cycloalkyl group, wherein when substituted, the substituent is selected from halogen or a cyano group;

$X_1$ is selected from a substituted or unsubstituted $C_1$-$C_{10}$ alkylidene group, a substituted or unsubstituted $C_2$-$C_{10}$ alkenylene group, =$R^c$=, or =$R^c$—, wherein $R^c$ is selected from a substituted or unsubstituted $C_2$-$C_6$ alkylidene group, and when substituted, a substituent is selected from halogen or a cyano group;

when $A_1$ is N, then $A_2$ is N—$R_3$ and/or $A_3$ is N;
when $A_3$ is N, then $A_2$ is N—$R_3$ and/or $A_1$ is N;
when $A_2$ is N—$R_3$, then at least one of $A_1$ or $A_3$ is N; and
a ring consisting of $A_1$, $A_2$, $A_3$ and $X_1$ is not a benzene ring.

In some embodiments, the compound of formula I includes at least one selected from the group consisting of:

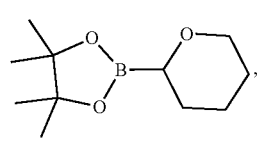

compound I-1

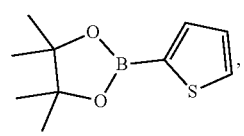

compound I-2

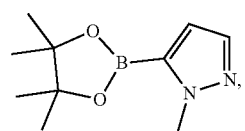

compound I-3

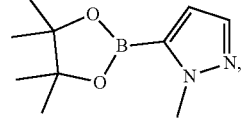

compound I-4

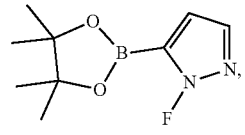

compound I-5

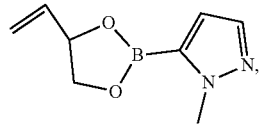

compound I-6

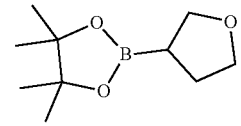

compound I-7

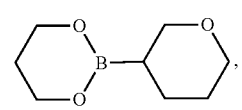

compound I-8

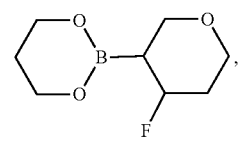

compound I-9

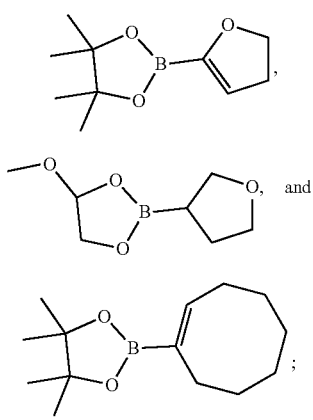

compound I-10 compound I-11 and a content of the compound of formula I accounts for 0.1% to 5% of a weight of the electrolyte.

In some embodiments, the electrolyte further includes lithium difluorophosphate, and a content of the lithium difluorophosphate accounts for 0.01% to 1.5% of a weight of the electrolyte.

In some embodiments, the content of the lithium difluorophosphate accounts for a % of the weight of the electrolyte, and a content of the compound of formula I accounts for b % of the weight of the electrolyte, where a range of a/b is 0.01-6.

In some embodiments, the electrolyte further includes a compound of formula II:

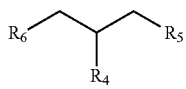

formula II where $R_4$, $R_5$ and $R_6$ are each independently selected from H, a cyano group, a substituted or unsubstituted $C_1$-$C_{10}$ alkyl group, or —$R^a$—X—$R^b$, where $R^a$ is selected from a single bonded or a substituted or unsubstituted $C_1$-$C_{10}$ alkylidene group, $R^b$ is selected from a cyano group, or a substituted or unsubstituted $C_1$-$C_{10}$ alkyl group, and X is selected from O, S, a sulfone group, or a carbonate group, where when substituted, the substituent is selected from halogen or a cyano group, and at least one of $R_4$, $R_5$, and $R_6$ includes a cyano group; and a content of the compound of formula II accounts for 0.1% to 5% of a weight of the electrolyte.

In some embodiments, the compound of formula II includes at least one selected from the group consisting of:

compound II-1

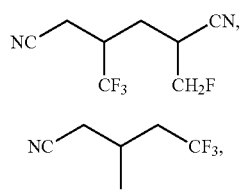

compound II-2 compound II-3

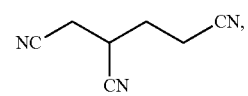

compound II-4

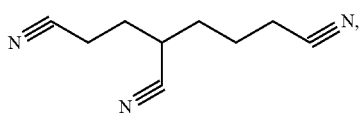

compound II-5

compound II-6

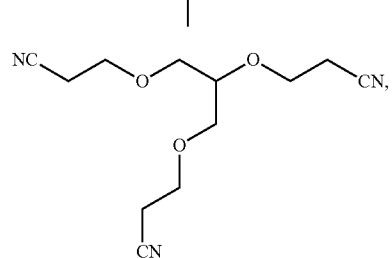

compound II-7

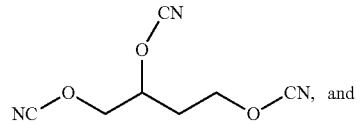

compound II-8

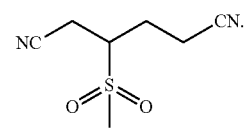

In some embodiments, the electrolyte further includes at least one selected from the group consisting of a compound of formula III, a compound of formula IV and a compound of formula V:

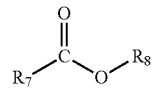

formula III

formula IV

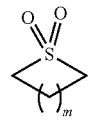

formula V where $R_7$ and $R_8$ are each independently selected from a $C_1$-$C_{10}$ alkyl group that is unsubstituted or substituted with one or more fluorine atoms, and at least one of $R_7$ and $R_8$ is substituted with fluorine;

$R_9$ and $R_{10}$ are each independently selected from a $C_1$-$C_{10}$ alkyl group that is unsubstituted or substituted with one or more fluorine atoms, and at least one of $R_9$ and $R_{10}$ is substituted with fluorine;

m is an integer ranging from 0 to 5; and based on a total weight of the electrolyte, a content of the compound of formula III is less than or equal to 60%;

based on the total weight of the electrolyte, a content of the compound of formula IV is less than or equal to 60%; and based on the total weight of the electrolyte, a content of the compound of formula V is less than or equal to 25%.

In some embodiments, the compound of formula III includes at least one selected from the group consisting of:

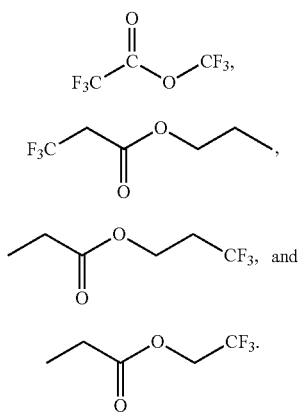

compound III-1 compound III-2 compound III-3 compound III-4

The compound of formula IV includes at least one selected from the group consisting of:

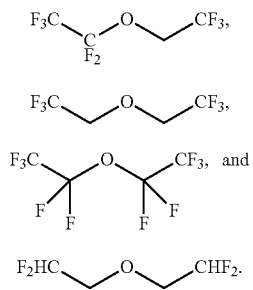

compound IV-1 compound IV-2 compound IV-3 compound IV-4

The compound of formula V includes: at least one of

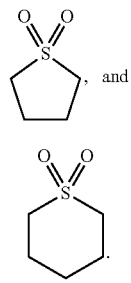

compound V-1 compound V-2

In another aspect, this application provides an electrochemical apparatus, including a positive electrode, a negative electrode, and any one of the foregoing electrolytes.

In some embodiments, the positive electrode includes a positive electrode material containing an aluminum element, and the aluminum element accounts for 0.001% to 3% of a total weight of the positive electrode material.

In yet another aspect, this application provides an electronic apparatus, and the electronic apparatus includes any one of the foregoing electrochemical apparatuses.

Additional aspects and advantages of the embodiments of the application are partially described and presented in the later description, or explained by implementation of the embodiments of the application.

BRIEF DESCRIPTION OF DRAWINGS

FIGURE shows infrared test results of a positive electrode surface of an embodiment and a reference example.

DETAILED DESCRIPTION

Embodiments of this application will be described in detail below. The embodiments of this application shall not be construed as a limitation on the protection scope claimed by this application. Unless otherwise specified, the following terms used herein have the meanings indicated below.

The term "approximately" used herein are intended to describe and represent small variations. When used in combination with an event or a circumstance, the term may refer to an example in which the exact event or circumstance occurs or an example in which an extremely similar event or circumstance occurs. For example, when used in combination with a value, the term may refer to a variation range of less than or equal to ±10% of the value, for example, less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. In addition, quantities, ratios, and other values are sometimes presented in the format of ranges in this specification. It should be understood that such range formats are used for convenience and simplicity and should be flexibly understood as including not only values clearly designated as falling within the range but also all individual values or sub-ranges covered by the range as if each value and sub-range were clearly designated.

In the description of embodiments and claims, a list of items preceded by the term "one of" may mean any one of the listed items. For example, if items A and B are listed, the phrase "one of A and B" means only A or only B. In another example, if items A, B, and C are listed, the phrase "one of A, B, and C" means only A, only B, or only C. The item A may contain a single element or a plurality of elements. The item B may contain a single element or a plurality of elements. The item C may contain a single element or a plurality of elements.

In the description of embodiments and claims, a list of items preceded by the terms such as "at least one of", "at least one type of" or other similar terms may mean any combination of the listed items. For example, if items A and B are listed, the phrase "at least one of A and B" or "at least one of A or B" means only A, only B, or A and B. In another example, if items A, B, and C are listed, the phrase "at least one of A, B, and C" or "at least one of A, B, or C" means only A, only B, only C, A and B (excluding C), A and C (excluding B), B and C (excluding A), or all of A, B, and C. The item A may contain a single element or a plurality of elements. The item B may contain a single element or a plurality of elements. The item C may contain a single element or a plurality of elements.

In the description of embodiments and claims, the carbon number, namely, the number after the capital letter "C", for example, "1", "3" or "10" in "$C_1$-$C_{10}$" and "$C_3$-$C_{10}$", represents the number of carbon atoms in a specific functional group. That is, the functional groups may include 1-10 carbon atoms and 3-10 carbon atoms, respectively. For example, "$C_1$-$C_4$ alkyl group" or "$C_{1-4}$ alkyl group" refers to an alkyl group having 1 to 4 carbon atoms, for example, $CH_3$—, $CH_3CH_2$—, $CH_3CH_2CH_2$—, $(CH_3)_2CH$—, $CH_3CH_2CH_2CH_2$—, $CH_3CH_2CH$ ($CH_3$)— or $(CH_3)_3C$—.

As used herein, the term "alkyl group" is intended to be a linear saturated hydrocarbon structure having 1 to 10 carbon atoms. The term "alkyl group" is also intended to be a branched or cyclic hydrocarbon structure having 3 to 8 carbon atoms. For example, an alkyl group may be an alkyl group having 1 to 8 carbon atoms, an alkyl group having 1 to 6 carbon atoms, an alkyl group having 1 to 5 carbon atoms, an alkyl group having 1 to 4 carbon atoms, or an alkyl group having 1 to 3 carbon atoms. References to an alkyl group with a specific carbon number are intended to cover all geometric isomers with the specific carbon number. Therefore, for example, "butyl" is meant to include n-butyl, sec-butyl, isobutyl, tert-butyl, and cyclobutyl; and "propyl" includes n-propyl, isopropyl, and cyclopropyl. Examples of alkyl groups include, but are not limited to, methyl, ethyl, n-propyl, isopropyl, cyclopropyl, n-butyl, isobutyl, sec-butyl, tert-butyl, cyclobutyl, n-pentyl, isopentyl, neopentyl, cyclopentyl, methylcyclopentyl, ethylcyclopentyl, n-hexyl, isohexyl, cyclohexyl, n-heptyl, octyl, cyclopropyl, cyclobutyl, norbornyl, and the like. In addition, the alkyl group may be arbitrarily substituted.

The term "alkenyl group" refers to a straight-chain or branched monovalent unsaturated hydrocarbon group having at least one and usually 1, 2, or 3 carbon-carbon double bonds. Unless otherwise defined, the alkenyl group generally contains 2 to 10 carbon atoms. For example, the alkenyl group may be an alkenyl group having 2 to 8 carbon atoms, an alkenyl group having 2 to 6 carbon atoms, or an alkenyl group having 2 to 4 carbon atoms. Representative alkenyl groups include, for example, vinyl, n-propenyl, isopropenyl, n-but-2-enyl, but-3-enyl, and n-hex-3-enyl. In addition, the alkenyl group may be arbitrarily substituted.

The term "alkoxy group" refers to an "alkyl-O—" group, where the term "alkyl" is as defined above. For example, the term "alkoxy group" covers an alkoxy group having 1 to 10 carbon atoms, an alkoxy group having 1 to 8 carbon atoms, an alkoxy group having 1 to 6 carbon atoms, an alkoxy group having 1 to 4 carbon atoms, or an alkoxy group having 5 to 8 carbon atoms. Representative examples of the alkoxy group include, but are not limited to, methoxy, ethoxy, propoxy, 2-propoxy, butoxy, tert-butoxy, pentyloxy and hexyloxy. In addition, the alkoxy group may be arbitrarily substituted.

The term "alkylidene group" means a linear or branched chain divalent saturated hydrocarbon group. For example, an alkylidene group may be an alkylidene group having 1 to 10 carbon atoms, an alkylidene group having 1 to 8 carbon atoms, an alkylidene group having 1 to 6 carbon atoms, or an alkylidene group having 1 to 4 carbon atoms. Representative alkylidene groups include, for example, methylene, ethane-1,2-diyl ("ethylene"), propane-1,2-diyl, propane-1,3-diyl, butane-1,4-diyl, and pentane-1,5-diyl. In addition, the alkylidene group may be arbitrarily substituted.

The term "alkyleneoxy group" means —O-alkylidene-, where the term "alkylidene" is as defined above.

The term "alkenylene group" covers linear and branched chain alkenylene groups. References to an alkenylene group with a specific carbon number are intended to cover all geometric isomers with the specific carbon number. For example, an alkenylene group may be an alkenylene group having 2 to 10 carbon atoms, an alkenylene group having 2 to 8 carbon atoms, an alkenylene group having 2 to 6 carbon atoms, or an alkenylene group having 2 to 4 carbon atoms. Representative alkenylene groups include, for example, vinylene, propenylene, and butenylene. In addition, the alkenylene group may be arbitrarily substituted.

The term "cycloalkyl group" covers cyclic alkyl groups. For example, a cycloalkyl group may be an cycloalkyl group having 3 to 10 carbon atoms, a cycloalkyl group having 3 to 8 carbon atoms, a cycloalkyl group having 3 to 6 carbon atoms, a cycloalkyl group having 3 to 5 carbon atoms, a cycloalkyl group having 5 to 7 carbon atoms, or a cycloalkyl group having 5 to 9 carbon atoms. In addition, the cycloalkyl group may be arbitrarily substituted.

When the foregoing substituents are substituted, unless otherwise specified, they are substituted with one or more halogens.

As used herein, the term "halogen" covers F, Cl, Br, and I, and is preferably F or $C_1$.

I. ELECTROLYTE

In one aspect, this application provides an electrolyte. In some embodiments, the electrolyte includes a compound of formula I:

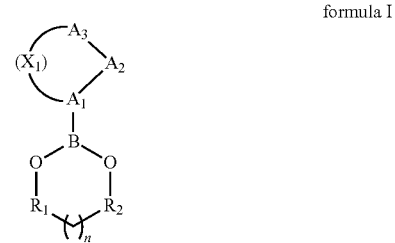

formula I where n is an integer ranging from 0 to 10;

$R_1$ and $R_2$ are each independently selected from a substituted or unsubstituted $C_1$-$C_{10}$ alkylidene group, a substituted or unsubstituted $C_2$-$C_{10}$ alkenylene group, or a substituted or unsubstituted $C_1$-$C_{10}$ alkyleneoxy group, where when substituted, the substituent is one or more selected from the group consisting of a $C_1$-$C_6$ alkyl group, a $C_2$-$C_6$ alkenyl group, a $C_1$-$C_6$ alkoxy group, halogen and a cyano group;

$A_1$ is selected from CH, C, N, S, O, B or Si;

$A_2$ is selected from CH—$R_3$, N—$R_3$, S, O, B—$R_3$ or SiH—$R_3$;

$A_3$ is selected from $CH_2$, CH, C, N, S, O, B or Si;

$R_3$ is selected from hydrogen, halogen, a substituted or unsubstituted $C_1$-$C_{10}$ alkyl group, or a substituted or unsubstituted $C_3$-$C_{10}$ cycloalkyl group, where when substituted, the substituent is selected from halogen or a cyano group;

$X_1$ is selected from a substituted or unsubstituted $C_1$-$C_{10}$ alkylidene group, a substituted or unsubstituted $C_2$-$C_{10}$ alkenylene group, =$R^c$=, or =$R^c$—, where $R^c$ is selected from a substituted or unsubstituted $C_2$-$C_6$ alkylidene group, and when substituted, a substituent is selected from halogen or a cyano group;

when $A_1$ is N, then $A_2$ is N—$R_3$ and/or $A_3$ is N;

when $A_3$ is N, then $A_2$ is N—$R_3$ and/or $A_1$ is N;

when $A_2$ is N—$R_3$, then at least one of $A_1$ or $A_3$ is N; and a ring consisting of $A_1$, $A_2$, $A_3$ and $X_1$ is not a benzene ring.

In some embodiments, n is an integer ranging from 0 to 8, an integer ranging from 0 to 6, or an integer ranging from 0 to 4. In some embodiments, n is 0, 1, 2 or 3. In some embodiments, n is 0 (that is, $R_1$ and $R_2$ are connected by a single bond).

In some embodiments, $R_1$ and $R_2$ are each independently selected from the following substituted or unsubstituted groups: a $C_1$-$C_8$ alkylidene group, a $C_1$-$C_6$ alkylidene group or a $C_1$-$C_4$ alkylidene group, a $C_2$-$C_8$ alkenylene group, a $C_2$-$C_6$ alkenylene group or a $C_2$-$C_4$ alkenylene group, or a $C_1$-$C_8$ alkyleneoxy group, a $C_1$-$C_6$ alkyleneoxy group or a $C_1$-$C_4$ alkyleneoxy group, where when substituted, substitution is performed with one or more substituents selected from a $C_1$-$C_4$ alkyl group, a $C_2$-$C_4$ alkenyl group, a $C_1$-$C_4$ alkoxy group, halogen or a cyano group.

In some embodiments, $R_1$ and $R_2$ are each independently selected from the following substituted or unsubstituted groups: a $C_1$-$C_4$ alkylidene group, a $C_2$-$C_4$ alkenylene group, or a $C_1$-$C_4$ alkyleneoxy group. In some embodiments, $R_1$ and $R_2$ are each independently selected from substituted or unsubstituted methylene, where when substituted, the substituent is one or more selected from methyl, ethyl, vinyl, methoxy or F.

In some embodiments, $A_1$ is selected from CH, C, N, S, O, B or Si; $A_2$ is selected from CH—$R_3$, N—$R_3$, S, O, B—$R_3$ or SiH—$R_3$; $A_3$ is selected from $CH_2$, CH, C, N, S, O, B or Si;

In some embodiments, $R_3$ is selected from hydrogen, halogen, or the following substituted or unsubstituted groups: a $C_1$-$C_8$ alkyl group, a $C_1$-$C_6$ alkyl group or a $C_1$-$C_4$ alkyl group, or a $C_3$-$C_8$ cycloalkyl group, a $C_3$-$C_6$ cycloalkyl group or a $C_3$-$C_4$ cycloalkyl group, where when substituted, the substituent is selected from halogen or a cyano group.

In some embodiments, $R_3$ is selected from hydrogen, F, methyl, or ethyl.

In some embodiments, $A_1$ is selected from CH, C, or N. In some embodiments, $A_2$ is selected from CH, N, S, or O. In some embodiments, $A_3$ is selected from $CH_2$, CH, N, S, or O.

In some embodiments, $X_1$ is selected from the following substituted or unsubstituted groups: a $C_1$-$C_8$ alkylidene group, a $C_1$-$C_6$ alkylidene group or a $C_1$-$C_4$ alkylidene group, a $C_2$-$C_8$ alkenylene group, a $C_2$-$C_6$ alkenylene group or a $C_2$-$C_4$ alkenylene group, or =$R^c$= or =$R^c$—, where $R^c$ is a $C_2$-$C_4$ alkylidene group, and when substituted, the substituent is selected from halogen or a cyano group.

In some embodiments, $X_1$ is selected from the following substituted or unsubstituted groups: ethylene, propylene, vinylene, ethylenediene (=CH—CH=), or =CH—$C_4H_8$—, where when substituted, substitution is performed with one or more F.

In some embodiments, the compound of formula I includes at least one selected from the group consisting of:

compound I-1
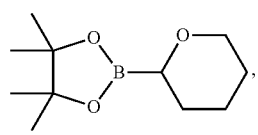

compound I-2
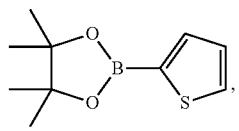

compound I-3
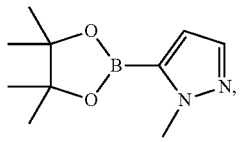

compound I-4
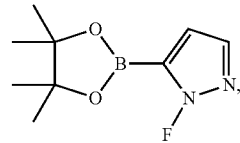

compound I-5
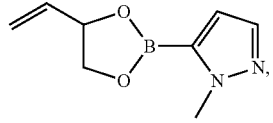

compound I-6
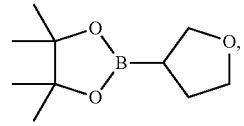

compound I-7
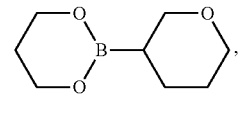

compound I-8
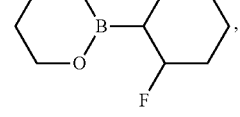

compound I-9
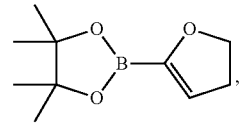

compound I-10
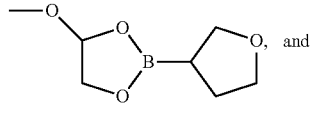

compound I-11
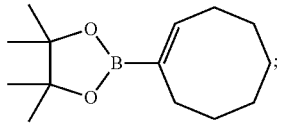

and a content of the compound of formula I accounts for 0.1% to 5% of a weight of the electrolyte.

In some embodiments, the content of the compound of formula I accounts for 0.5% to 4.5% or 0.5% to 2.5% of the weight of the electrolyte. In some embodiments, the content of the compound of formula I accounts for approximately 0.1%, approximately 0.5%, approximately 1%, approximately 1.5%, approximately 2%, approximately 2.5%, approximately 3%, approximately 3.5%, approximately 4%, approximately 4.5%, or approximately 5% of the weight of the electrolyte.

In some embodiments, the electrolyte further includes lithium difluorophosphate, and a content of the lithium difluorophosphate accounts for 0.01% to 1.5% of the weight of the electrolyte.

In some embodiments, the content of the lithium difluorophosphate accounts for a % of the weight of the electrolyte, and the content of the compound of formula I accounts for b % of the weight of the electrolyte, where a range of a/b is 0.01-6. In some embodiments, the electrolyte further includes lithium difluorophosphate, and a content of the lithium difluorophosphate accounts for 0.1% to 1% or 0.1% to 0.5% of the weight of the electrolyte. In some embodiments, the content of the lithium difluorophosphate accounts for approximately 0.1%, approximately 0.2%, approximately 0.3%, approximately 0.4%, approximately 0.5%, approximately 0.6%, approximately 0.7%, approximately 0.8%, approximately 0.9%, approximately 1%, approximately 1.1%, approximately 1.2%, approximately 1.3%, approximately 1.4%, or approximately 1.5% of the weight of the electrolyte.

In some embodiments, a weight ratio a/b of the lithium difluorophosphate to the compound of formula I ranges from 0.02 to 4. In some embodiments, the weight ratio a/b of the lithium difluorophosphate to the compound of formula I is 1:90, 1:80, 1:70, 1:60, 1:50, 1:40, 1:30, 1:20, 1:10, 1:5, 1:2, 1:1, 2:1, 3:1, 4:1 or 5:1. In some embodiments, the weight ratio of the lithium difluorophosphate to the compound of formula I is 1:5, 3:5, 1:1, 1:1.5, or 3:1.

In some embodiments, the electrolyte further includes a compound of formula II:

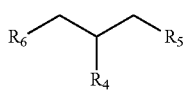

formula II where $R_4$, $R_5$ and $R_6$ each are independently selected from H, a cyano group, a substituted or unsubstituted $C_1$-$C_{10}$ alkyl group, or —$R^a$—X—$R^b$, where $R^a$ is selected from a single bonded or a substituted or unsubstituted $C_1$-$C_{10}$ alkylidene group, $R^b$ is selected from a cyano group, or a substituted or unsubstituted $C_1$-$C_{10}$ alkyl group, and X is selected from O, S, a sulfone group, or a carbonate group, where when substituted, a substituent is selected from halogen or a cyano group, and at least one of $R_4$, $R_5$, and $R_6$ includes a cyano group; and a content of the compound of formula II accounts for 0.1% to 5% of a weight of the electrolyte.

In some embodiments, $R_4$, $R_5$ and $R_6$ are each independently selected from: H, a cyano group, the following substituted or unsubstituted groups: a $C_1$-$C_8$ alkyl group, a $C_1$-$C_6$ alkyl group, or a $C_1$-$C_4$ alkyl group, or —$R^a$—X—$R^b$, where W is selected from a single bond, or the following substituted or unsubstituted groups: a $C_1$-$C_8$ alkylidene group, a $C_1$-$C_6$ alkylidene group, or a $C_1$-$C_4$ alkylidene group, $R^b$ is selected from a cyano group, or the following substituted or unsubstituted groups: a $C_1$-$C_8$ alkyl group, a $C_1$-$C_6$ alkyl group, or a $C_1$-$C_4$ alkyl group, and X is selected from O, S, a sulfone group, or a carbonate group, and at least one of $R_4$, $R_5$, and $R_6$ includes a cyano group.

In some embodiments, $R_4$, $R_5$, and $R_6$ are each independently selected from: H, a cyano group, the following substituted or unsubstituted groups: methyl, ethyl, or propyl, or —$R^a$—X—$R^b$, where $R^a$ is selected from a single bond, or the following substituted or unsubstituted groups: methylene, ethylene or propylene, $R^b$ is selected from a cyano group, or the following substituted or unsubstituted groups: methyl, ethyl, or propyl, and X is selected from O, S or a sulfone group, and at least one of $R_4$, $R_5$, and $R_6$ includes a cyano group.

In some embodiments, the content of the compound of formula II accounts for 0.5% to 4.5% or 0.5% to 2.5% of the weight of the electrolyte. In some embodiments, the content of the compound of formula II accounts for approximately 0.1%, approximately 0.3%, approximately 0.5%, approximately 1%, approximately 1.5%, approximately 2%, approximately 2.5%, approximately 3%, approximately 3.5%, approximately 4%, approximately 4.5%, or approximately 5% of the weight of the electrolyte.

In some embodiments, the compound of formula II includes at least one selected from the group consisting of:

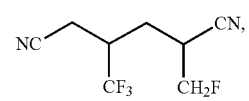

compound II-1

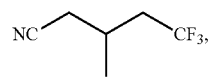

compound II-2

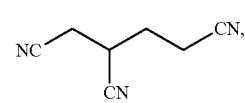

compound II-3

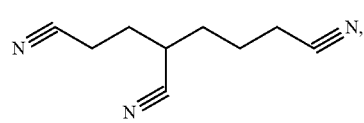

compound II-4

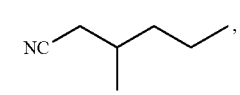

compound II-5

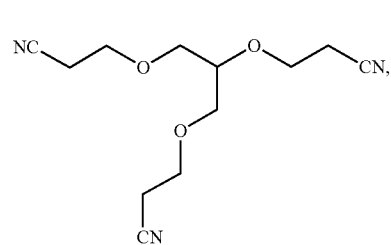

compound II-6

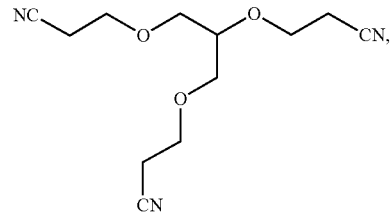

compound II-7

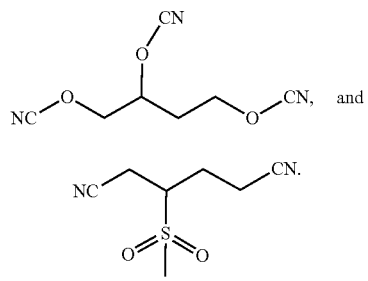

compound II-8

In some embodiments, the electrolyte further includes at least one selected from the group consisting of a compound of formula III, a compound of formula IV and a compound of formula V:

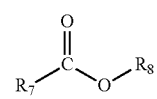

formula III

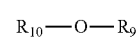

formula IV formula V

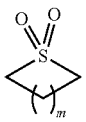

where $R_7$ and $R_8$ are each independently selected from a $C_1$-$C_{10}$ alkyl group that is unsubstituted or substituted with one or more fluorine atoms, and at least one of $R_7$ and $R_8$ is substituted with fluorine;

$R_9$ and $R_{10}$ are each independently selected from a $C_1$-$C_{10}$ alkyl group that is unsubstituted or substituted with one or more fluorine atoms, and at least one of $R_9$ and $R_{10}$ is substituted with fluorine;

m is an integer ranging from 0 to 5; and based on a total weight of the electrolyte, a content of the compound of formula III is less than or equal to 60%;

based on the total weight of the electrolyte, a content of the compound of formula IV is less than or equal to 60%; and based on the total weight of the electrolyte, a content of the compound of formula V is less than or equal to 25%.

In some embodiments, $R_7$ and $R_8$ are each independently selected from the following groups that are unsubstituted or substituted with one or more fluorine atoms: a $C_1$-$C_8$ alkyl group, a $C_1$-$C_6$ alkyl group, or a $C_1$-$C_4$ alkyl group, and at least one of $R_7$ and $R_8$ is substituted with fluorine. In some embodiments, $R_7$ and $R_8$ are each independently selected from methyl, ethyl, propyl, —$CHF_2$, —$CH_2F$, —$CF_3$, —$CH_2CF_3$, —$CHFCF_3$, —$CF_2CF_3$, or —$CH_2CH_2CF_3$, and at least one of $R_7$ and $R_8$ is substituted with fluorine.

In some embodiments, $R_9$ and $R_{10}$ are each independently selected from the following groups that are unsubstituted or substituted with one or more fluorine atoms: a $C_1$-$C_8$ alkyl group, a $C_1$-$C_6$ alkyl group, or a $C_1$-$C_4$ alkyl group, and at least one of $R_9$ and $R_{10}$ is substituted with fluorine. In some embodiments, $R_9$ and $R_{10}$ are each independently selected from methyl, ethyl, propyl, —$CHF_2$, —$CH_2F$, —$CF_3$, —$CH_2CF_3$, —$CHFCF_3$, —$CF_2CF_3$, or —$CH_2CH_2CF_3$, and at least one of $R_9$ and $R_{10}$ is substituted with fluorine.

In some embodiments, m is an integer ranging from 0 to 5; in some embodiments, m is 0, 1, 2 or 3; and in some embodiments, m is 0 (that is, a single bond exists in the parentheses of formula V).

In some embodiments, the content of the compound of formula III accounts for 3% to 60% or 10% to 50% of a weight of the electrolyte. In some embodiments, the content of the compound of formula III accounts for approximately 1%, approximately 3%, approximately 5%, approximately 10%, approximately 15%, approximately 20%, approximately 25%, approximately 30%, approximately 35%, approximately 40%, approximately 45%, approximately 50%, approximately 55%, or approximately 60% of the weight of the electrolyte.

In some embodiments, the content of the compound of formula IV accounts for 3% to 60% or 10% to 50% of a weight of the electrolyte. In some embodiments, the content of the compound of formula IV accounts for approximately 1%, approximately 3%, approximately 5%, approximately 10%, approximately 15%, approximately 20%, approximately 25%, approximately 30%, approximately 35%, approximately 40%, approximately 45%, approximately 50%, approximately 55%, or approximately 60% of the weight of the electrolyte.

In some embodiments, the content of the compound of formula V accounts for 5% to 20% of a weight of the electrolyte. In some embodiments, the content of the compound of formula V accounts for approximately 1%, approximately 3%, approximately 5%, approximately 10%, approximately 15%, approximately 20%, or approximately 25% of the weight of the electrolyte.

In some embodiments, the compound of formula III includes at least one selected from the group consisting of:

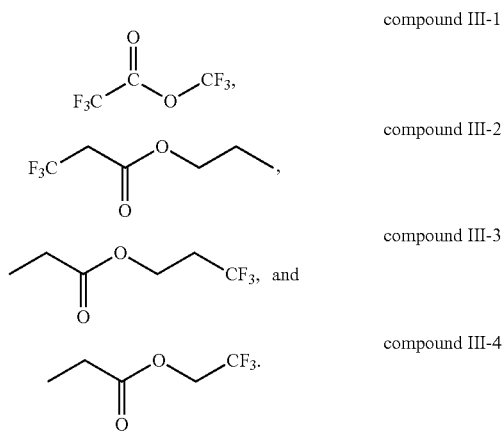

The compound of formula IV includes at least one selected from the group consisting of:

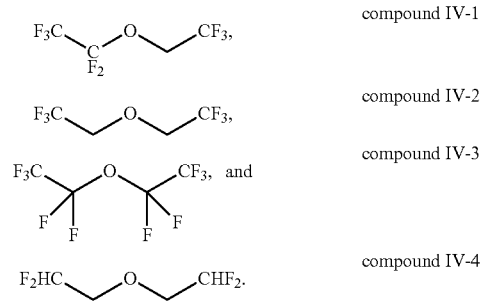

The compound of formula V includes: at least one of

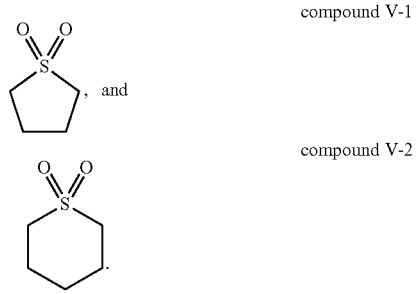

In some embodiments, the electrolyte further includes a lithium salt and an organic solvent.

In some embodiments, the lithium salt includes or is selected from at least one of an organic lithium salt or an inorganic lithium salt. In some embodiments, the lithium salt of this application contains at least one of fluorine, boron, and phosphorus.

In some embodiments, the lithium salt includes at least one of lithium hexafluorophosphate, lithium bistrifluoromethanesulfonimide, lithium bis(fluorosulfonyl)imide, lithium 4,5-dicyano-2-trifluoromethylimidazole, and lithium perchlorate, and further preferably, the lithium salt is selected from lithium hexafluorophosphate ($LiPF_6$).

In some embodiments, a concentration of the lithium salt in the electrolyte of this application is: 0.6 mol/L to 2 mol/L or 0.8 mol/L to 1.2 mol/L.

In some embodiments, the organic solvent may include linear carbonate, cyclic carbonate, linear carboxylate, cyclic carboxylate, and the like. For example, the organic solvent may include one or more of dimethyl carbonate, ethyl methyl carbonate, methyl propyl carbonate, methyl isopropyl carbonate, methyl butyl carbonate, diethyl carbonate, dipropyl carbonate, dibutyl carbonate, ethylene carbonate, propylene carbonate, butylene carbonate, methyl acetate, ethyl acetate, propyl acetate, butyl acetate, methyl propionate, ethyl propionate, propyl propionate, butyl propionate, methyl butyrate, ethyl butyrate, propyl butyrate, methyl valerate, ethyl valerate, methyl pivalate, ethyl pivalate, butyl pivalate, γ-butyrolactone, and γ-valerolactone. In some embodiments, the organic solvent may include one or more of ethylene carbonate, propylene carbonate, diethyl carbonate, methyl ethyl carbonate, and dimethyl carbonate.

In some embodiments, the organic solvent accounts for 70% to 90% of the weight of the electrolyte.

II. ELECTROCHEMICAL APPARATUS

The electrochemical apparatus according to this application includes any apparatus in which an electrochemical reaction takes place. Specific examples of the apparatus include all kinds of primary batteries, secondary batteries, fuel batteries, solar batteries, or capacitors. Especially, the electrochemical apparatus is a lithium secondary battery, including a lithium metal secondary battery, a lithium-ion secondary battery, a lithium polymer secondary battery, or a lithium-ion polymer secondary battery. In some embodiments, the electrochemical apparatus according to this application is an electrochemical apparatus provided with a positive electrode having a positive-electrode active material capable of occluding and releasing metal ions, and a negative electrode having a negative electrode active material capable of occluding and releasing metal ions. The electrochemical apparatus includes any one of the foregoing electrolytes in this application.

Electrolyte

An electrolyte used in the electrochemical apparatus according to this application is any one of the foregoing electrolytes in this application. In addition, the electrolyte used in the electrochemical apparatus according to this application may also include other electrolytes within the scope not departing from the essence of this application.

Negative Electrode

A negative electrode of the electrochemical apparatus according to the embodiments of this application includes a current collector and a negative electrode active material layer formed on the current collector. The negative electrode active material is not limited to a specific type, and may be selected based on needs. The negative electrode active material layer includes a negative-electrode active material, and the negative electrode active material may include a material that reversibly intercalates or deintercalates a lithium ion, lithium metal, a lithium metal alloy, a material capable of doping or dedoping lithium, or a transition metal oxide.

The material that reversibly intercalates and deintercalates a lithium ion may be a carbon material. The carbon material may be any carbon-based negative-electrode active material commonly used in a lithium-ion rechargeable electrochemical apparatus. Examples of the carbon material include crystalline carbon, amorphous carbon, and combinations thereof. The crystalline carbon may be amorphous or plate-shaped, flake-shaped, spherical or fiber-shaped natural graphite or artificial graphite. The amorphous carbon may be soft carbon, hard carbon, a mesophase pitch carbonization product, burnt coke, or the like. Both low crystalline carbon and high crystalline carbon can be used as the carbon material. The low crystalline carbon material may generally include soft carbon and hard carbon. The high crystalline carbon material may generally include natural graphite, crystalline graphite, pyrolytic carbon, a mesophase pitch-based carbon fiber, mesophase carbon microbeads, mesophase pitch, and high-temperature calcined carbon (such as petroleum or coke derived from coal tar pitch).

In some embodiments, the negative-electrode active material is selected from one or more of natural graphite, artificial graphite, mesocarbon microbeads (MCMB for short), hard carbon, soft carbon, silicon, a silicon-carbon composite, a Li—Sn alloy, a Li—Sn—O alloy, Sn, SnO, $SnO_2$, spinel-structure lithiated $TiO_2$—$Li_4Ti_5O_{12}$, and a Li—Al alloy.

The negative-electrode active material layer includes a binder, and the binder may include various binder polymers, for example, polyvinyl alcohol, carboxymethyl cellulose, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly (1,1-difluoroethylene), polyethylene, polypropylene, styrene-butadiene rubber, acrylic styrene-butadiene rubber, epoxy resin, and nylon.

The negative-electrode active material layer further includes a conductive material to improve electrode conductivity. Any conductive material that causes no chemical change can be used as the conductive material. Examples of the conductive material include: a carbon-based material such as natural graphite, artificial graphite, carbon black, acetylene black, Ketjen black, and carbon fiber; a metal-based material such as metal powder or metal fiber including copper, nickel, aluminum, silver; a conductive polymer such as a polyphenylene derivative; or any mixture thereof.

The current collector may be copper foil, nickel foil, stainless steel foil, titanium foil, nickel foam, copper foam, a polymer substrate coated with a conductive metal, or a combination thereof.

In some embodiments, the current collector includes, but is not limited to: copper foil, nickel foil, stainless steel foil, titanium foil, nickel foam, copper foam, a polymer substrate coated with a conductive metal, and any combination thereof.

The negative electrode can be prepared by using a preparation method known in the art. For example, the negative electrode may be obtained by using the following method: mixing an active material, a conductive material, and a binder in a solvent to prepare an active material composition, and coating the active material composition on a current collector.

Positive Electrode

A positive electrode of the electrochemical apparatus according to the embodiments of this application includes a current collector and a positive-electrode active material layer provided on the current collector.

In some embodiments, the positive-electrode active material includes a compound that reversibly intercalates and deintercalates a lithium ion (namely, a lithiated intercalation compound). The active material that can intercalate and deintercalate lithium may be a lithium cobalt oxide, a lithium nickel cobalt manganate, a lithium nickel cobalt aluminate, a lithium manganate oxide, a lithium manganese iron phosphate, a lithium vanadium phosphate, a lithium vanadyl phosphate, a lithium iron phosphate, and a lithium titanate, a lithium-rich manganese-based material, or an active material coated or doped with such active material as the base.

In some embodiments, the positive electrode includes a positive electrode material containing an aluminum element, and the aluminum element accounts for 0.001% to 3% of a total weight of the positive electrode material.

In some embodiments, the positive-electrode active material layer further includes a binder, and optionally, further includes a conductive material. The binder enhances binding between particles of the positive-electrode active material, and binding between the positive-electrode active material and the current collector. Non-limiting examples of the binder include: polyvinyl alcohol, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly (1,1-difluoroethylene), polyethylene, polypropylene, styrene-butadiene rubber, acrylic styrene-butadiene rubber, epoxy resin, and nylon.

In some embodiments, the conductive material imparts conductivity to the electrode. The conductive material may include any conductive material that causes no chemical change. Non-limiting examples of the conductive material include: a carbon-based material (for example, natural graphite, artificial graphite, carbon black, acetylene black, Ketjen black, and carbon fiber), a metal-based material (for example, metal powder, and metal fiber, including copper, nickel, aluminum, silver, and the like), a conductive polymer (for example, a polyphenylene derivative), and any mixture thereof.

The current collector may be, but is not limited to, aluminum (Al).

Separator

In some embodiments, the electrochemical apparatus according to this application has a separator disposed between the positive electrode and the negative electrode to prevent short circuit. The separator used in the electrochemical apparatus according to this application is not particularly limited to any material or shape, and may be based on any technology disclosed in the prior art. In some embodiments, the separator includes a polymer or an inorganic substance formed by a material stable to the electrolyte of this application.

For example, the separator may include a substrate layer and a surface treatment layer. The substrate layer is a non-woven fabric, membrane, or composite membrane having a porous structure, and a material of the substrate layer is selected from at least one of polyethylene, polypropylene, polyethylene terephthalate, and polyimide. Specifically, a polypropylene porous membrane, a polyethylene porous membrane, polypropylene nonwoven fabric, polyethylene nonwoven fabric, or polypropylene-polyethylene-polypropylene porous composite membrane can be selected.

The surface treatment layer is provided on at least one surface of the substrate layer, and the surface treatment layer may be a polymer layer or an inorganic layer, or may be a layer formed by a mixed polymer and an inorganic substance.

The inorganic layer includes inorganic particles and a binder. The inorganic particles are selected from one or a combination of aluminum oxide, silicon oxide, magnesium oxide, titanium oxide, hafnium oxide, tin oxide, ceria oxide, nickel oxide, zinc oxide, calcium oxide, zirconium oxide, yttrium oxide, silicon carbide, boehmite, aluminum hydroxide, magnesium hydroxide, calcium hydroxide, and barium sulfate. The binder is selected from one or a combination of a polyvinylidene fluoride, a vinylidene fluoride-hexafluoropropylene copolymer, a polyamide, a polyacrylonitrile, a polyacrylate, a polyacrylic acid, a polyacrylate, a polyvinylpyrrolidone, a polyvinyl ether, a polymethyl methacrylate, a polytetrafluoroethylene, and a polyhexafluoropropylene.

The polymer layer includes a polymer, and a material of the polymer is selected from at least one of a polyamide, a polyacrylonitrile, an acrylate polymer, a polyacrylic acid, a polyacrylate, a polyvinylpyrrolidone, a polyvinyl ether, a polyvinylidene fluoride, and a poly(vinylidene fluoride-hexafluoropropylene).

III. APPLICATION

The electrolyte according to the embodiments of this application can improve the high-temperature cycle performance, high-temperature storage performance and kinetics of an electrochemical apparatus, and has higher safety, so that the electrochemical apparatus manufactured according to this application is applicable to electronic devices in various fields.

The electrochemical apparatus according to this application is not particularly limited to any purpose, and may be used for any known purposes. For example, the electrochemical apparatus may be used for a notebook computer, a pen-input computer, a mobile computer, an electronic book player, a portable telephone, a portable fax machine, a portable copier, a portable printer, a headset, a video recorder, a liquid crystal television, a portable cleaner, a portable CD player, a mini-disc, a transceiver, an electronic notebook, a calculator, a storage card, a portable recorder, a radio, a standby power source, a motor, an automobile, a motorcycle, a motor bicycle, a bicycle, a lighting appliance, a toy, a game console, a clock, an electric tool, a flash lamp, a camera, a large household battery, a lithium ion capacitor, or the like.

IV. EMBODIMENTS

Below, this application will be further specifically described with embodiments and reference examples, and this application is not limited to these embodiments as long as the essence of this application is not changed.

1. Preparation of a Lithium-Ion Battery (1) Preparation of a Negative Electrode

Mix graphite, styrene-butadiene rubber (SBR), and sodium carboxymethyl cellulose (CMC) in an appropriate amount of deionized water solvent at a weight ratio of 95:2:3 by stirring to form a uniform negative electrode slurry; and coat the slurry on copper foil of a negative electrode current collector, dry the slurry, perform cold pressing, and weld tabs to obtain the negative electrode.

(2) Preparation of a Positive Electrode i. Preparation of the Positive Electrode Using a Positive-Electrode Active Material without Aluminum Doped Mix lithium cobalt oxide (LiCoO$_2$), conductive carbon (Super p), and polyvinylidene fluoride (whose weight-average molecular weight Mw is 85 W and whose molecular weight distribution Mw/Mn is 2.0) in a weight ratio of 95:2:3, add N-methylpyrrolidone (NMP), stir under the action of a vacuum mixer until the system becomes a uniform positive electrode slurry, and then evenly coat the positive electrode slurry on aluminum foil of a positive electrode current collector; and after drying the positive electrode slurry at 85° C., perform cold pressing, cutting, and slitting, weld tabs and dry under vacuum at 85° C. for 4 hours to obtain the positive electrode.

ii. Preparation of the Positive Electrode Using a Positive-Electrode Active Material with Aluminum Doped Mix lithium cobalt oxide with aluminum doped, conductive carbon (Super p), and polyvinylidene fluoride (whose weight-average molecular weight Mw is 85 W and whose molecular weight distribution Mw/Mn is 2.0) in a weight ratio of 95:2:3, add N-methylpyrrolidone (NMP), stir under the action of a vacuum mixer until the system becomes a uniform positive electrode slurry, and then evenly coat the positive electrode slurry on aluminum foil of a positive electrode current collector; and after drying the positive electrode slurry at 85° C., perform cold pressing, cutting, and slitting, weld tabs and dry under vacuum at 85° C. for 4 hours to obtain the positive electrode.

The foregoing lithium cobalt oxide with aluminum doped is obtained by using the following method: mixing lithium cobalt oxide (LiCoO$_2$) without aluminum doped and aluminum oxide (Al$_2$O$_3$), where an added amount of aluminum accounts for X % of the moles of cobalt in the lithium cobalt oxide, a value of X is less than or equal to 3, and ethanol is used as a dispersant; after mixing, dry the ethanol and sinter the dried ethanol in a tube furnace at 500° C. for 4 hours; and after sintering, natural cool the ethanol to obtain black powder, where the black powder is the lithium cobalt oxide doped with different amounts of aluminum.

(3) Preparation of an Electrolyte

In an glove box under argon atmosphere with a water content less than 10 ppm, mix ethylene carbonate (EC), propylene carbonate (PC), and diethyl carbonate (DEC) evenly at a mass ratio of 1:1:1, add LiPF$_6$ to dissolve and stir evenly to form a basic electrolyte, where a concentration of LiPF$_6$ is 1.15 mol/L. Types and amounts of added substances are shown in the following tables, and a content of each substance is a mass percentage calculated based on a total mass of the electrolyte.

(4) Preparation of a Separator

Use an 8-micron thick polyethylene (PE) separator.

(5) Preparation of the Lithium-Ion Battery

Lay the positive electrode, separator, and negative electrode in order, so that the separator is between the positive electrode and the negative electrode for isolation, and then wind and place the laid positive electrode, separator, and negative electrode in an aluminum foil bag. Inject the prepared electrolyte into a vacuum-dried battery to complete the preparation of the lithium-ion battery after processes such as vacuum packaging, standing, chemical conversion, and forming.

2. Performance Test of the Lithium-Ion Battery (1) High-Temperature Storage Performance Test of the Lithium-Ion Battery Let the lithium-ion battery stand for 30 minutes at 25° C., charge the lithium-ion battery to 4.53 V at a constant current rate of 0.5 C, and then charge the lithium-ion battery to 0.05 C at a constant voltage of 4.53 V. Let the lithium-ion battery stand for 5 minutes, store the lithium-ion battery at 85° C. for 8 hours or at 60° C. for 24 days, and then measure battery thickness of the battery and calculate the battery thickness expansion rate by using the following formula:

$$\text{Thickness expansion rate}=[(\text{Thickness after storage}-\text{Thickness before storage})/\text{Thickness before storage}]\times 100\%.$$

(2) Cycle Performance Test of the Lithium-Ion Battery at 45° C.

At 45° C., charge the lithium-ion battery to 4.53 V at a constant current of 0.5 C, then charge the lithium-ion battery to a current of 0.05 C at a constant voltage, and discharge the lithium-ion battery to 3.0 V at a constant current of 0.5 C. This is the first cycle. Cycle the foregoing steps for the lithium-ion battery many times under the foregoing conditions. The first discharge capacity is taken as 100%. Repeat the charge and discharge cycle until the discharge capacity decays to 80%, stop the test, and record the number of cycles as an indicator to evaluate the cycle performance of the lithium-ion battery.

(3) Positive Electrode Surface Test

After the foregoing forming process of preparation of the lithium-ion battery is completed, disassemble the battery in an glove box under argon atmosphere with a water content less than 10 ppm, take part of the positive electrode, rinse the taken out positive electrode with dimethyl carbonate (DMC) to clean remaining lithium salt on the surface, and then dry the surface for sample preparation. Use a Fourier transform infrared spectrometer to test the surface of the positive electrode.

(4) Test of H$_2$O Content and HF Content in the Electrolyte

As in the foregoing preparation method of the lithium-ion battery, before injecting the prepared electrolyte into the vacuum-dried battery, take about and seal 20 ml of the electrolyte. A moisture test is mainly carried out by using an AKD-A7 intelligent micro-moisture analyzer. An error is ±3 micrograms when a water content is less than 10 micrograms per gram of sample, and an error is ±5 micrograms when the water content is between 10 micrograms and 500 micrograms per gram of sample.

The HF content in the foregoing electrolyte is determined by an acid-base titration method. A triethylamine standard solution is used to titrate free acid in the electrolyte, and a result is expressed in grams of HF contained in each gram of sample.

A. Electrolytes and lithium-ion batteries of samples S$_{I-1}$ to S$_{I-16}$ were prepared according to the foregoing method, where the positive electrodes of all samples were positive electrodes prepared using a positive-electrode active material without aluminum doped. For electrolyte composition and test results, see Table 1 and Table 2.

TABLE 1

| Sample name | Compound of formula I Structural formula | Compound of formula I Content (%) | Number of cycles at 45° C. | Storage thickness expansion rate at 85° C. | Storage thickness expansion rate at 60° C. |
|---|---|---|---|---|---|
| $S_{I-1}$ | / | / | 290 | 25.20% | 10.60% |
| $S_{I-2}$ | Compound 1-1 | 0.5 | 343 | 15.70% | 8.40% |
| $S_{I-3}$ | Compound 1-2 | 0.5 | 350 | 15.20% | 8.00% |
| $S_{I-4}$ | Compound 1-3 | 0.1 | 319 | 16.20% | 9.40% |
| $S_{I-5}$ | Compound 1-3 | 0.3 | 346 | 15.10% | 8.30% |
| $S_{I-6}$ | Compound 1-3 | 0.5 | 365 | 14.80% | 7.80% |
| $S_{I-7}$ | Compound 1-3 | 1 | 354 | 14.20% | 7.40% |
| $S_{I-8}$ | Compound 1-3 | 1.5 | 342 | 13.80% | 6.90% |
| $S_{I-9}$ | Compound 1-3 | 2 | 338 | 14.00% | 7.60% |
| $S_{I-10}$ | Compound 1-3 | 3 | 324 | 14.10% | 8.00% |
| $S_{I-11}$ | Compound 1-3 | 4 | 315 | 16.40% | 8.70% |
| $S_{I-12}$ | Compound 1-3 | 5 | 299 | 18.70% | 9.30% |
| $S_{I-13}$ | Compound 1-5 | 0.5 | 357 | 15.30% | 8.00% |
| $S_{I-14}$ | Compound 1-6 | 0.2 | 339 | 15.90% | 9.20% |
| $S_{I-15}$ | Compound 1-8 | 0.3 | 349 | 15.70% | 8.90% |
| $S_{I-16}$ | Compound 1-9 | 1 | 350 | 14.80% | 7.80% |

Note:
"/" indicates not added.

Table 1 demonstrates the effect on battery performance when different contents of the compound of formula I are added in the electrolyte. By comparing sample $S_{I-1}$ (reference example) with other samples in Table 1, it can be seen that introduction of a specific content of the compound of formula I in the electrolyte can improve the high-temperature cycle performance and high-temperature storage performance. Without wishing to be bound by any theory, it is believed that the foregoing improvement may be mainly due to the fact that boron ions stabilize oxygen free radicals in the lithium cobalt oxide, inhibiting structural collapse and crystal structure change of the positive electrode material.

TABLE 2

| Sample name | H$_2$O content (μg/g) | HF content (μg/g) |
|---|---|---|
| $S_{I-1}$ | 30 | 70 |
| $S_{I-2}$ | 22 | 45 |
| $S_{I-3}$ | 25 | 47 |
| $S_{I-4}$ | 29 | 54 |
| $S_{I-5}$ | 27 | 51 |
| $S_{I-6}$ | 23 | 42 |
| $S_{I-7}$ | 20 | 38 |
| $S_{I-8}$ | 20 | 43 |
| $S_{I-9}$ | 22 | 46 |
| $S_{I-10}$ | 26 | 49 |
| $S_{I-11}$ | 25 | 51 |
| $S_{I-12}$ | 21 | 42 |
| $S_{I-13}$ | 24 | 46 |
| $S_{I-14}$ | 28 | 50 |
| $S_{I-15}$ | 26 | 48 |
| $S_{I-16}$ | 24 | 47 |

Table 2 demonstrates the effect on the H$_2$O content and HF content in the electrolyte when the compound of formula I is added in the electrolyte. It can be seen from the comparison between the electrolyte of sample $S_{I-1}$ (reference example) and the electrolytes of other samples in the table that the addition of the compound of formula I can significantly reduce the contents of H$_2$O and HF in the electrolyte, which can effectively reduce damage by HF in the electrolyte to the interface of positive and negative electrodes and improve the overall stability of the battery, thereby improving the high-temperature storage performance and high-temperature cycle performance of the battery.

B. Electrolytes and lithium-ion batteries of samples $S_{II-1}$ to $S_{II-5}$ were prepared according to the foregoing method, where the positive electrodes of all samples were positive electrodes prepared using a positive-electrode active material without aluminum doped. For electrolyte composition and test results, see Table 3.

TABLE 3

| Sample name | Compound I-3 (%) | Lithium difluoro- phosphate (%) | Number of cycles at 45° C. | Storage thickness expansion rate at 85° C. | Storage thickness expansion rate at 60° C |
|---|---|---|---|---|---|
| $S_{I-6}$ | 0.5 | / | 365 | 14.8% | 7.8% |
| $S_{II-1}$ | 0.5 | 0.1 | 397 | 13.8% | 7.3% |
| $S_{II-2}$ | 0.5 | 0.3 | 435 | 10.9% | 5.3% |
| $S_{II-3}$ | 0.3 | 0.3 | 410 | 11.5% | 6.0% |
| $S_{II-4}$ | 0.5 | 0.5 | 380 | 12.0% | 7.0% |
| $S_{II-5}$ | 1.5 | 0.3 | 378 | 11.5% | 6.7% |

Note:
"/" indicates not added.

Table 3 shows the effect on battery performance when the compound of formula I is combined with different contents of lithium difluorophosphate. Adding a specific amount of lithium difluorophosphate to an electrolyte containing the compound of formula I can further improve the high-temperature cycle performance and high-temperature storage performance of the battery. This improvement may be due to a fact that an appropriate amount of lithium difluorophosphate inhibits the decomposition of lithium hexafluorophosphate in the electrolyte.

C. Electrolytes and lithium-ion batteries of samples $S_{III-1}$ to $S_{III-19}$ were prepared according to the foregoing method, where the positive electrodes of all samples were positive electrodes prepared using a positive-electrode active material without aluminum doped. For electrolyte composition and test results, see Table 4.

TABLE 4

| Sample name | Compound of formula I Compound I-3 (%) | Compound of formula II Structure | Compound of formula II Content (%) | Number of cycles at 45° C. | Storage thickness expansion rate at 85° C. | Storage thickness expansion rate at 60° C. |
|---|---|---|---|---|---|---|
| $S_{I-6}$ | 0.5 | / | 0 | 365 | 14.80% | 7.80% |
| $S_{III-1}$ | 0.5 | Compound II-1 | 0.5 | 400 | 9.00% | 7.00% |
| $S_{III-2}$ | 0.5 |  | 1 | 433 | 7.00% | 5.00% |

TABLE 4-continued

| Sample name | Compound of formula I<br>Compound I-3 (%) | Compound of formula II<br>Structure | Content (%) | Number of cycles at 45° C. | Storage thickness expansion rate at 85° C. | Storage thickness expansion rate at 60° C. |
|---|---|---|---|---|---|---|
| $S_{III-3}$ | 0.5 | | 1.5 | 464 | 6.70% | 4.80% |
| $S_{III-4}$ | 0.5 | | 2 | 443 | 6.30% | 4.70% |
| $S_{III-5}$ | 0.5 | | 2.5 | 426 | 6.00% | 4.50% |
| $S_{III-6}$ | 0.5 | | 5 | 359 | 8.00% | 7.00% |
| $S_{III-7}$ | 0.5 | Compound II-3 | 1.5 | 467 | 8.40% | 7.60% |
| $S_{III-8}$ | 0.5 | Compound II-4 | 0.1 | 357 | 12.50% | 7.50% |
| $S_{III-9}$ | 0.5 | | 0.5 | 408 | 9.60% | 7.20% |
| $S_{III-10}$ | 0.5 | | 1 | 445 | 8.70% | 6.70% |
| $S_{III-11}$ | 0.5 | | 1.5 | 465 | 7.50% | 5.80% |
| $S_{III-12}$ | 0.3 | | 1.5 | 452 | 8.00% | 6.40% |
| $S_{III-13}$ | 0.5 | | 2 | 448 | 6.80% | 6.10% |
| $S_{III-14}$ | 0.5 | | 3 | 437 | 6.30% | 5.70% |
| $S_{III-15}$ | 0.5 | | 3.5 | 421 | 5.90% | 5.40% |
| $S_{III-16}$ | 0.5 | | 4 | 375 | 6.50% | 6.00% |
| $S_{III-17}$ | 0.5 | | 5 | 354 | 7.80% | 7.00% |
| $S_{III-18}$ | 0.5 | Compound II-5 | 1 | 459 | 7.80% | 6.50% |
| $S_{III-19}$ | 0.5 | Compound II-6 | 1.5 | 448 | 7.50% | 5.70% |

Note:
"/" indicates not added.

Table 4 shows the effect on battery performance when the compound of formula I is combined with the compound of formula II. The further inclusion of the compound of formula II in the electrolyte containing the compound of formula I can further improve the high-temperature cycle performance and high-temperature storage performance of the battery. The main reason for this improvement may be that the nitrile compound is complexed with the high-valent cobalt in the positive-electrode active material, which stabilizes the cobalt ion in the positive-electrode active material and inhibits dissolution of the cobalt ion in the electrolyte, thereby effectively inhibiting structural collapse and crystal structure change of the positive-electrode active material.

D. Electrolytes and lithium-ion batteries of samples $S_{V-1}$ to $S_{V-38}$ were prepared according to the foregoing method, where the positive electrodes of all samples were positive electrodes prepared using a positive-electrode active material without aluminum doped. For electrolyte composition and test results, see Table 5.

TABLE 5

| Sample name | Compound I-3 (%) | Compound of formula III | Compound of formula IV | Compound of formula V | Compound content of formula III, formula IV and/or formula V (%) | Number of cycles at 45° C. | Storage thickness expansion rate at 85° C. | Storage thickness expansion rate at 60° C. |
|---|---|---|---|---|---|---|---|---|
| $S_{I-6}$ | 0.5 | / | / | / | / | 365 | 14.80% | 7.80% |
| $S_{V-1}$ | 0.5 | Compound III-1 | / | / | 3 | 378 | 13.50% | 7.40% |
| $S_{V-2}$ | 0.5 | | / | / | 5 | 382 | 12.40% | 6.90% |
| $S_{V-3}$ | 0.5 | | / | / | 10 | 455 | 11.30% | 6.20% |
| $S_{V-4}$ | 0.3 | | / | / | 15 | 437 | 10.70% | 5.80% |
| $S_{V-5}$ | 0.5 | | / | / | 30 | 426 | 9.80% | 5.50% |
| $S_{V-6}$ | 0.5 | | / | / | 60 | 362 | 10.60% | 6.30% |
| $S_{V-7}$ | 0.5 | Compound III-2 | / | / | 8 | 457 | 9.40% | 5.30% |
| $S_{V-8}$ | 0.5 | Compound III-3 | / | / | 5 | 380 | 12.10% | 7.20% |
| $S_{V-9}$ | 1.5 | | / | / | 10 | 420 | 11.70% | 6.80% |
| $S_{V-10}$ | 0.5 | | / | / | 10 | 467 | 8.30% | 5.10% |
| $S_{V-11}$ | 0.5 | | / | / | 15 | 453 | 8.70% | 6.40% |
| $S_{V-12}$ | 0.5 | | / | / | 20 | 443 | 9.00% | 6.60% |
| $S_{V-13}$ | 0.5 | | / | / | 30 | 432 | 10.30% | 6.70% |
| $S_{V-14}$ | 0.5 | | / | / | 35 | 426 | 10.80% | 6.90% |
| $S_{V-15}$ | 0.5 | | / | / | 45 | 387 | 11.70% | 7.20% |
| $S_{V-16}$ | 0.5 | | / | / | 60 | 349 | 12.50% | 7.60% |
| $S_{V-17}$ | 0.5 | / | Compound IV-1 | / | 3 | 382 | 13.20% | 7.50% |
| $S_{V-18}$ | 0.5 | / | | / | 10 | 440 | 10.50% | 5.80% |
| $S_{V-19}$ | 0.5 | / | Compound IV-2 | / | 5 | 389 | 12.60% | 7.30% |
| $S_{V-20}$ | 0.5 | / | | / | 10 | 438 | 10.30% | 6.80% |
| $S_{V-21}$ | 0.5 | / | | / | 15 | 429 | 10.70% | 7.10% |
| $S_{V-22}$ | 0.5 | / | | / | 25 | 417 | 11.60% | 7.50% |

TABLE 5-continued

| Sample name | Compound I-3 (%) | Compound of formula III | Compound of formula IV | Compound of formula V | Compound content of formula III, formula IV and/or formula V (%) | Number of cycles at 45° C. | Storage thickness expansion rate at 85° C. | Storage thickness expansion rate at 60° C. |
|---|---|---|---|---|---|---|---|---|
| $S_{V-23}$ | 0.5 | / | | / | 45 | 379 | 12.90% | 7.80% |
| $S_{V-24}$ | 0.5 | / | | / | 60 | 347 | 13.10% | 8.20% |
| $S_{V-25}$ | 0.5 | | Compound IV-3 | / | 10 | 435 | 10.27% | 6.76% |
| $S_{V-26}$ | 0.5 | | Compound IV-4 | / | 10 | 430 | 10.35% | 6.87% |
| $S_{V-27}$ | 0.5 | / | / | Compound V-1 | 3 | 376 | 13.70% | 7.60% |
| $S_{V-28}$ | 0.5 | / | / | | 5 | 420 | 12.50% | 7.00% |
| $S_{V-29}$ | 0.5 | / | / | | 10 | 458 | 10.70% | 6.50% |
| $S_{V-30}$ | 0.3 | / | / | | 10 | 447 | 11.40% | 6.70% |
| $S_{V-31}$ | 0.5 | / | / | | 15 | 439 | 12.60% | 7.30% |
| $S_{V-32}$ | 0.5 | / | / | | 20 | 387 | 13.00% | 7.70% |
| $S_{V-33}$ | 0.5 | / | / | | 25 | 346 | 13.80% | 7.90% |
| $S_{V-34}$ | 0.5 | / | / | Compound V-2 | 10 | 445 | 10.90% | 6.80% |
| $S_{V-35}$ | 0.5 | Compound III-3 | Compound IV-1 | / | 10% compound III-3 + 10% compound IV-1 | 465 | 9.80% | 6.30% |
| $S_{V-36}$ | 0.5 | Compound III-3 | / | Compound V-1 | 10% compound III-3 + 10% compound V-1 | 473 | 8.70% | 5.70% |
| $S_{V-37}$ | 0.5 | / | Compound IV-1 | Compound V-1 | 10% compound IV-1 + 10% compound V-1 | 453 | 9.20% | 6.70% |
| $S_{V-38}$ | 0.5 | Compound III-3 | Compound IV-1 | Compound V-1 | 10% compound III-3 + 10% compound IV-1 + 10% compound V-1 | 435 | 9.50% | 6.90% |

Note:

"/" indicates not added.

Table 5 shows the effect of the combination of the compound of formula I and the compound of formula III, IV and/or formula V on battery performance. From the experimental results, it can be seen that the combination of the compound of formula I and an appropriate amount of the compound of formula III, IV and/or formula V can improve the battery cycle performance and high-temperature storage performance. This improvement may include the following reasons: the fluorine contained in the compound of formula III or formula IV has strong electronegativity and weak polarity, causing that formula III or formula IV has a higher dielectric constant and a better conductivity; formula III or formula IV has better wettability, lower HOMO and LUMO, better oxidation resistance, and high stability, so that electrolyte consumption during the cycle is reduced; the sulfone compound of formula V has higher pressure oxidation resistance, so that consumption of solvent during the cycle can be effectively reduced in the high voltage system, and an SEI film can be effectively formed on the negative electrode.

E. Electrolytes and lithium-ion batteries of samples $S_{VI-1}$ to $S_{VI-12}$ were prepared according to the foregoing method, where the positive electrodes of samples $S_{VI-1}$ to $S_{VI-12}$ were prepared using a positive-electrode active material with aluminum doped. For electrolyte composition and test results, see Table 6.

TABLE 6

| Sample name | Compound I-3 (%) | Percentage of aluminum doping amount in the number of moles of cobalt in lithium cobalt oxide (%) | Number of cycles at 45° C. | Storage thickness expansion rate at 85° C. | Storage thickness expansion rate at 60° C. |
|---|---|---|---|---|---|
| $S_{I-6}$ | 0.5 | / | 365 | 14.8% | 7.8% |
| $S_{VI-1}$ | 0.5 | 0.1 | 370 | 14.3% | 7.2% |
| $S_{VI-2}$ | 0.5 | 0.3 | 386 | 13.8% | 6.9% |
| $S_{VI-3}$ | 0.5 | 0.5 | 408 | 13.1% | 6.3% |
| $S_{VI-4}$ | 0.5 | 1 | 432 | 12.7% | 5.8% |
| $S_{VI-5}$ | 0.5 | 1.5 | 456 | 11.3% | 5.6% |
| $S_{VI-6}$ | 0.3 | 1.5 | 448 | 10.2% | 5.3% |
| $S_{VI-7}$ | 0.5 | 2 | 437 | 9.8% | 4.8% |
| $S_{VI-8}$ | 0.5 | 2.5 | 429 | 10.4% | 5.6% |
| $S_{VI-9}$ | 1.5 | 3 | 364 | 10.7% | 6.1% |
| $S_{VI-10}$ | 0.5 | 3 | 372 | 11.3% | 6.8% |
| $S_{VI-11}$ | 0.5 | 4 | 352 | 13.1% | 7.4% |
| $S_{VI-12}$ | 0.5 | 4.5 | 307 | 14.2% | 8.7% |

Note:
"/" indicates not added.

Table 6 shows the effect on battery performance when the positive electrode includes lithium cobalt oxide doped with different amounts of aluminum. It can be seen from the experimental results that the use of an electrolyte containing the compound of formula I in the battery and an appropriate amount of aluminum-doped lithium cobalt oxide in the positive electrode can improve the high-temperature cycle performance and high-temperature storage performance of the battery. This improvement may include the following reasons: substituting cobalt with an appropriate amount of aluminum can stabilize the crystal structure change of the positive electrode during the delithiation process, and inhibit structural collapse and crystal structure change of the positive-electrode active material, thereby improving the cycle stability of the battery. As the amount of aluminum doping increases, it has a certain impact on the unit cell parameters in the crystal structure of lithium cobalt oxide. The value of a decreases, the value of c increases, and the ratio of c/a increases linearly with the amount of aluminum doping. The layered property of the material is more obvious, which is more conducive to transmission of lithium ions, and improves the thermal stability of the positive electrode material, thereby improving the high-temperature storage performance of the battery.

F. Electrolytes and lithium-ion batteries of samples $S_{VII-1}$ to $S_{VII-28}$ were prepared according to the foregoing method, where the electrolyte composition, positive electrode composition and test results are shown in Table 7.

IV, compound of formula V and/or lithium cobaltate doped with aluminum. It can be seen from the experimental results that the further combination of at least two of the foregoing elements with the electrolyte containing the compound of formula I has some advantages compared with the combination of the compound of formula I with only one of the foregoing elements.

The combination of the compound of formula I and the positive-electrode active material doped with aluminum significantly improves the cycle performance and high-temperature storage performance of the battery. This improvement may be mainly because the compound of formula I helps to improve the stability of the positive electrode interface and reduce the oxidative decomposition and consumption of the electrolyte at the interface. The doping of aluminum promotes internal stability of the positive electrode material and provides a stable positive electrode structure for the battery during the high-temperature cycle process, thereby significantly improving the high-temperature cycle and high-temperature storage performance of the battery. On the basis of the compound of formula I and the positive-electrode active material doped with aluminum, further adding at least one additive of lithium difluorophosphate, compound of formula II, compound of formula III, compound of formula IV, or compound

TABLE 7

| Sample name | Compound I-3 (%) | Lithium difluoro-phosphate (%) | Compound II-4 (%) | Compound III-4 (%) | Compound IV-3 (%) | Compound V-1 (%) | Percentage of aluminum doping amount in the number of moles of cobalt in lithium cobalt oxide (%) | Number of cycles at 45° C. | Storage thickness expansion rate at 85° C. | Storage thickness expansion rate at 60° C. |
|---|---|---|---|---|---|---|---|---|---|---|
| $S_{I-6}$ | 0.5 | / | / | / | / | / | 0 | 365 | 14.8% | 7.8% |
| $S_{II-2}$ | 0.5 | 0.3 | / | / | / | / | 0 | 435 | 10.9% | 5.3% |
| $S_{VII-1}$ | 0.5 | 0.3 | 1 | / | / | / | 0 | 452 | 10.0% | 8.0% |
| $S_{VII-2}$ | 0.5 | 0.3 | / | 10 | / | / | 0 | 464 | 7.9% | 5.2% |
| $S_{VII-3}$ | 0.5 | 0.3 | / | / | 10 | / | 0 | 462 | 8.0% | 5.4% |
| $S_{VII-4}$ | 0.5 | 0.3 | / | / | / | 10 | 0 | 458 | 7.8% | 5.1% |
| $S_{VII-5}$ | 0.5 | 0.3 | / | / | / | / | 1.5 | 471 | 7.6% | 4.8% |
| $S_{IV-6}$ | 0.5 | / | 1 | / | / | / | 0 | 445 | 8.7% | 6.7% |
| $S_{VII-6}$ | 0.5 | / | 1 | 10 | / | / | 0 | 463 | 8.0% | 5.3% |
| $S_{VII-7}$ | 0.5 | / | 1 | / | 10 | / | 0 | 460 | 8.2% | 5.2% |
| $S_{VII-8}$ | 0.5 | / | 1 | / | / | 10 | 0 | 458 | 8.2% | 5.3% |
| $S_{VII-9}$ | 0.5 | / | 1 | / | / | / | 1.5 | 468 | 7.7% | 4.9% |
| $S_{VII-10}$ | 0.5 | / | / | 10 | / | / | 1.5 | 465 | 7.5% | 4.7% |
| $S_{VII-11}$ | 0.5 | / | / | / | 10 | / | 1.5 | 460 | 7.6% | 4.9% |
| $S_{VII-12}$ | 0.5 | / | / | / | / | 10 | 1.5 | 462 | 7.5% | 5.0% |
| $S_{VII-13}$ | 0.5 | 0.3 | 1 | 10 | / | / | 0 | 476 | 7.2% | 4.6% |
| $S_{VII-14}$ | 0.5 | 0.3 | 2 | / | 10 | / | 0 | 472 | 7.3% | 4.8% |
| $S_{VII-15}$ | 0.5 | 0.3 | 1 | / | / | 10 | 0 | 469 | 7.5% | 5.1% |
| $S_{VII-16}$ | 0.5 | 0.3 | 1 | / | / | / | 1.5 | 481 | 7.0% | 4.3% |
| $S_{VII-17}$ | 0.5 | 0.3 | / | 10 | 10 | / | 0 | 471 | 7.6% | 5.3% |
| $S_{VII-18}$ | 0.5 | 0.3 | / | 12 | / | 10 | 0 | 469 | 7.9% | 5.5% |
| $S_{VII-19}$ | 0.5 | 0.3 | / | 10 | / | / | 1.5 | 478 | 7.2% | 4.8% |
| $S_{VII-20}$ | 0.5 | 0.3 | / | / | 10 | 10 | 0 | 473 | 7.5% | 5.2% |
| $S_{VII-21}$ | 0.5 | 0.3 | / | / | 10 | / | 1.5 | 483 | 6.9% | 4.8% |
| $S_{VII-22}$ | 0.5 | 0.3 | / | / | / | 8 | 1.5 | 480 | 7.2% | 5.0% |
| $S_{VII-23}$ | 0.5 | 0.3 | 1 | 10 | 10 | / | 0 | 483 | 6.8% | 4.9% |
| $S_{VII-24}$ | 0.5 | 0.3 | 1 | 10 | / | 10 | 0 | 479 | 6.9% | 5.1% |
| $S_{VII-25}$ | 0.5 | 0.3 | 1 | 10 | / | / | 1.5 | 495 | 6.7% | 4.6% |
| $S_{VII-26}$ | 0.5 | 0.3 | 1 | 10 | 12 | 10 | 0 | 487 | 6.8% | 4.8% |
| $S_{VII-27}$ | 0.5 | 0.3 | 1 | 10 | 10 | / | 1.5 | 492 | 6.9% | 5.0% |
| $S_{VII-28}$ | 0.5 | 0.3 | 1 | 10 | 10 | 10 | 1.5 | 452 | 7.3% | 5.7% |

Note:
"/" indicates not added.

Table 7 shows the effect on battery performance when the compound of formula I is combined with the following elements: lithium difluorophosphate, fluorine compound of formula I, compound of formula III, compound of formula IV, compound of formula V to the electrolyte also can improve the cycle performance of the battery. On the one hand, this may be due to the relatively stable structure of the positive electrode itself; on the other hand, it may be that the foregoing additives are not easily oxidized on the surface of the positive electrode, which reduces the further consumption of electrolyte and ensures that the battery has enough electrolyte during the cycle, thereby providing stable power for transmission of lithium ions.

From the foregoing embodiments, it can be found that the compound of general formula I is combined with any technical element or a plurality of technical elements. The boron ion in the compound of general formula I can stabilize the oxygen free radicals in lithium cobalt oxide, effectively inhibiting structural collapse and crystal structure change of the positive electrode material. In addition, a stable CEI film is formed on the surface of the positive electrode, which inhibits the oxidation of the electrolyte on the surface of the positive electrode material, improves the stability of the electrolyte, and effectively improves the cycle stability and high-temperature storage performance of the battery.

G. Infrared Test of Positive Electrode Surface

FIGURE shows a comparison of the infrared test results of the positive electrode of the sample $S_{I-1}$ and the positive electrode of the sample $S_{I-2}$. It can be seen from the FIGURE that the absorption vibration peaks of the two samples at about 2274 $cm^{-1}$ are significantly different, which indicates that addition of the compound I affects consumption of the electrolyte on the surface of the positive electrode during the chemical conversion, ensuring that the electrolyte has more sufficient film-forming additives in the later cycle process.

The above are only a few embodiments of this application, which do not limit this application in any form. Although this application is disclosed as above with preferred embodiments, the embodiments are not intended to limit this application. Changes or modifications made by those skilled in the art using the technical content disclosed above without departing from the scope of the technical solution of this application are considered as equivalent embodiments and fall within the scope of the technical solution.

References to "some embodiments", "an embodiment", "another example", "examples", "specific examples", or "some examples" in the specification mean the inclusion of specific features, structures, materials, or characteristics described in the embodiment or example in at least one embodiment or example of the application. Accordingly, descriptions appearing in the specification, such as "in some embodiments", "in the embodiments", "in an embodiment", "in another example", "in an example", "in a particular example", or "for example", are not necessarily references to the same embodiments or examples in the application. In addition, specific features, structures, materials, or characteristics herein may be incorporated in any suitable manner into one or more embodiments or examples. Although illustrative embodiments have been demonstrated and described, those skilled in the art should understand that the above embodiments are not to be construed as limiting the application, and that the embodiments may be changed, replaced, and modified without departing from the spirit, principle, and scope of the application.

What is claimed is:

1. An electrolyte comprising at least one compound selected from the group consisting of:

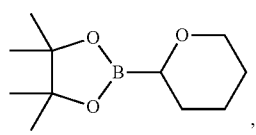

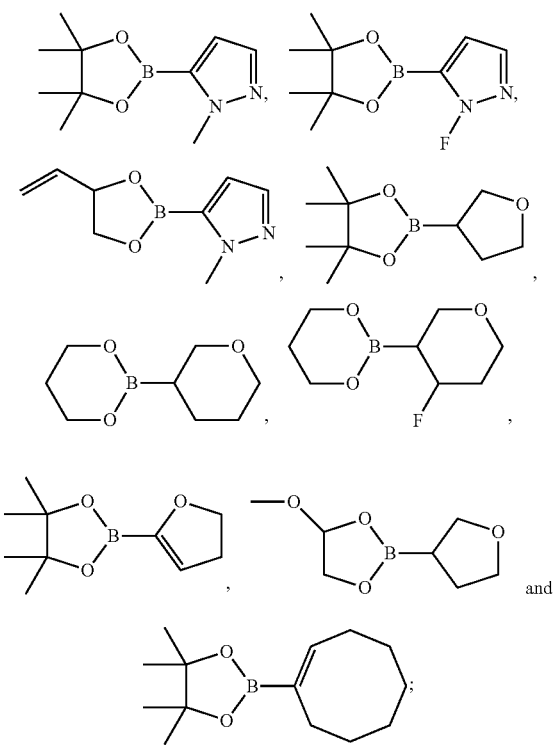

a content of the at least one compound accounts for b % of a weight of the electrolyte, wherein b % is 0.1% to 5%; and lithium difluorophosphate;

a content of the lithium difluorophosphate accounts for a % of the weight of the electrolyte;

wherein a range of a/b is 0.01-6.

2. The electrolyte according to claim 1, wherein the content of the lithium difluorophosphate accounts for 0.01% to 1.5% of a weight of the electrolyte.

3. The electrolyte according to claim 1, wherein the electrolyte further comprises a compound of formula II,

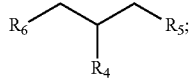

formula II wherein $R_4$, $R_5$ and $R_6$ are each independently selected from H, a cyano group, a substituted or unsubstituted $C_1$-$C_{10}$ alkyl group, or —$R^a$—X—$R^b$, wherein $R^a$ is selected from a single bonded or a substituted or unsubstituted $C_1$-$C_{10}$ alkylidene group, $R^b$ is selected from a cyano group, or a substituted or unsubstituted $C_1$-$C_{10}$ alkyl group, and X is selected from O, S, a sulfone group, or a carbonate group, wherein when substituted, the substituent is selected from halogen or a cyano group, and at least one of $R_4$, $R_5$, and $R_6$ comprises a cyano group; and a content of the compound of formula II accounts for 0.1% to 5% of a weight of the electrolyte.

4. The electrolyte according to claim 3, wherein the compound of formula II comprises at least one selected from the group consisting of:

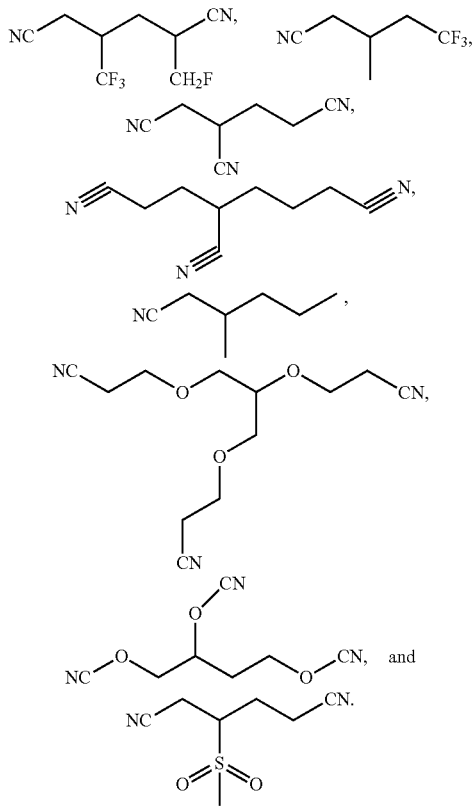

5. The electrolyte according to claim 1, further comprising at least one selected from the group consisting of a compound of formula III, a compound of formula IV and a compound of formula V:

$$R_7 \overset{\overset{O}{\|}}{C} O R_8 \quad \text{formula III}$$

$$R_{10}-O-R_9 \quad \text{formula IV}$$

formula V

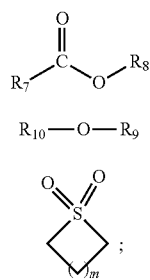

wherein $R_7$ and $R_8$ are each independently selected from a $C_1$-$C_{10}$ alkyl group that is unsubstituted or substituted with one or more fluorine atoms, and at least one of $R_7$ and $R_8$ is substituted with fluorine;
$R_9$ and $R_{10}$ are each independently selected from a $C_1$-$C_{10}$ alkyl group that is unsubstituted or substituted with one or more fluorine atoms, and at least one of $R_9$ and $R_{10}$ is substituted with fluorine;
m is an integer ranging from 0 to 5; and
a content of the compound of formula III accounts for less than or equal to 60% of a weight of the electrolyte,
a content of the compound of formula IV accounts for less than or equal to 60% of the weight of the electrolyte, and
a content of the compound of formula V accounts for less than or equal to 25% of the weight of the electrolyte.

6. The electrolyte according to claim 5, wherein
the compound of formula III comprises at least one selected from the group consisting of:

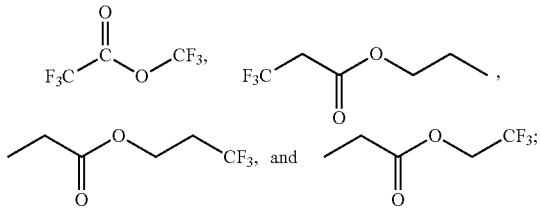

the compound of formula IV comprises at least one selected from the group consisting of:

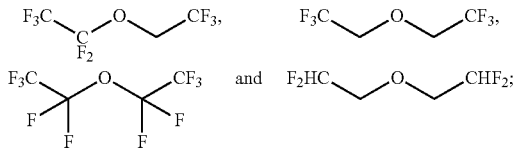

and
the compound of formula V comprises at least one of

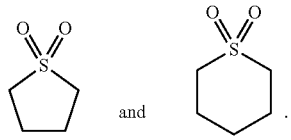 [SMILES: O=S1(=O)CCCC1 ; O=S1(=O)CCCCC1]

7. An electrochemical apparatus, comprising a positive electrode, a negative electrode, and an electrolyte comprising at least one compound selected from the group consisting of:

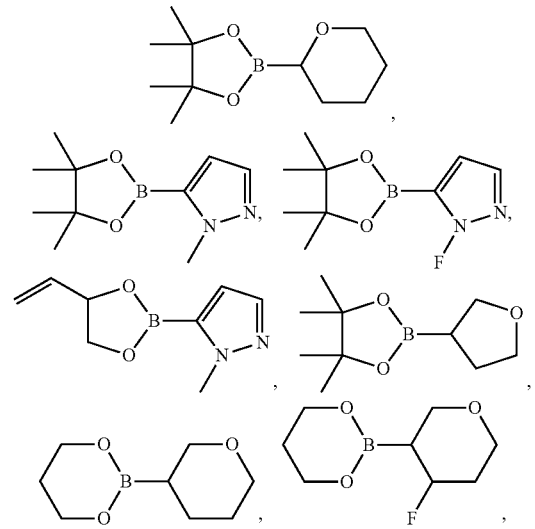

-continued

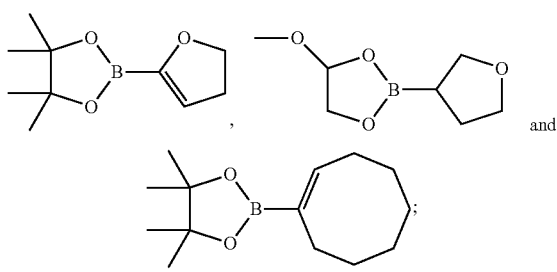
and a content of the at least one compound accounts for b % of a weight of the electrolyte, wherein b % is 0.1% to 5%; and lithium difluorophosphate;

a content of the lithium difluorophosphate accounts for a % of the weight of the electrolyte;

wherein a range of a/b is 0.01-6.

8. The electrochemical apparatus according to claim 7, wherein the electrolyte further comprises a compound of formula II,

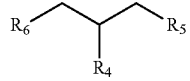

formula II wherein $R_4$, $R_8$ and $R_6$ are each independently selected from H, a cyano group, a substituted or unsubstituted $C_1$-$C_{10}$ alkyl group, or —$R^a$—X—$R^b$, wherein $R^a$ is selected from a single bonded or a substituted or unsubstituted $C_1$-$C_{10}$ alkylidene group, $R^b$ is selected from a cyano group, or a substituted or unsubstituted $C_1$-$C_{10}$ alkyl group, and X is selected from O, S, a sulfone group, or a carbonate group, wherein when substituted, the substituent is selected from halogen or a cyano group, and at least one of $R_4$, $R_5$, and $R_6$ comprises a cyano group; and a content of the compound of formula II accounts for 0.1% to 5% of a weight of the electrolyte.

9. The electrochemical apparatus according to claim 7, wherein the compound of formula II comprises at least one selected from the group consisting of:

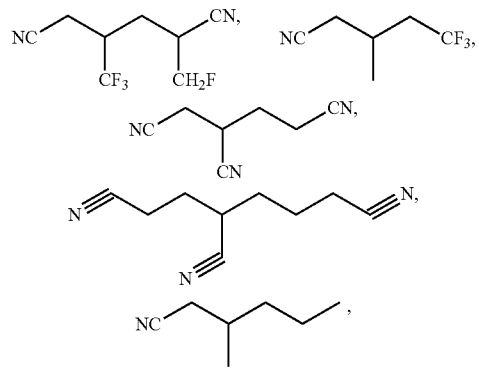

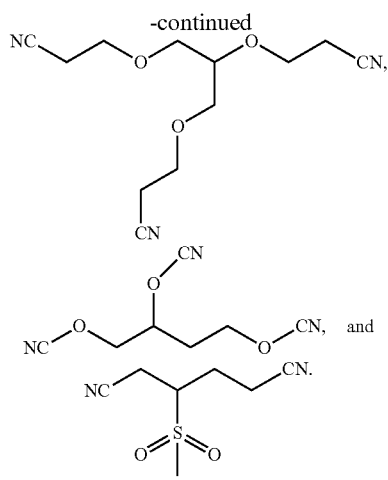

10. The electrochemical apparatus according to claim 7, wherein the electrolyte further comprising at least one of selected from the group consisting a compound of formula III, a compound of formula IV and a compound of formula V:

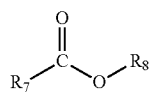

formula III

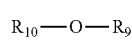

formula IV

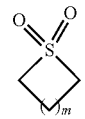

formula V wherein $R_7$ and $R_8$ are each independently selected from a $C_1$-$C_{10}$ alkyl group that is unsubstituted or substituted with one or more fluorine atoms, and at least one of $R_7$ and $R_8$ is substituted with fluorine;

$R_9$ and $R_{10}$ are each independently selected from a $C_1$-$C_{10}$ alkyl group that is unsubstituted or substituted with one or more fluorine atoms, and at least one of $R_9$ and $R_{10}$ is substituted with fluorine;

m is an integer ranging from 0 to 5; and a content of the compound of formula III accounts for less than or equal to 60% of a weight of the electrolyte, a content of the compound of formula IV accounts for less than or equal to 60% of the weight of the electrolyte, and a content of the compound of formula V accounts for less than or equal to 25% of the weight of the electrolyte.

11. The electrochemical apparatus according to claim 10, wherein the compound of formula III comprises at least one selected from the group consisting of:

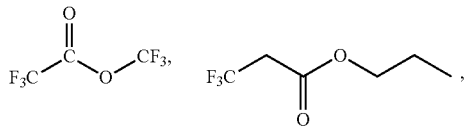

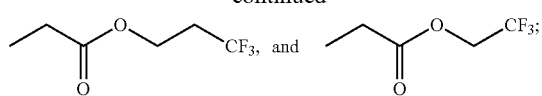

the compound of formula IV comprises at least one selected from the group consisting of:

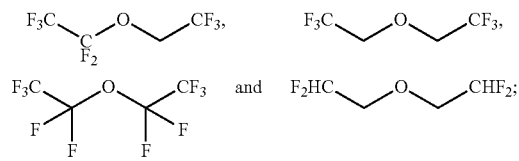

and
the compound of formula V comprises at least one of

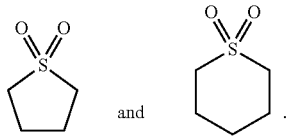 [SMILES: O=S1(=O)CCCC1 ; O=S1(=O)CCCCC1]

12. The electrochemical apparatus according to claim 7, wherein the positive-electrode comprises a positive-electrode active material containing an aluminum element, and the aluminum element accounts for 0.001% to 3% of a total weight of the positive-electrode active material.

13. An electronic apparatus, comprising an electrochemical apparatus, wherein the electrochemical apparatus, comprising a positive electrode, a negative electrode, and an electrolyte comprising at least one compound selected from the group consisting of

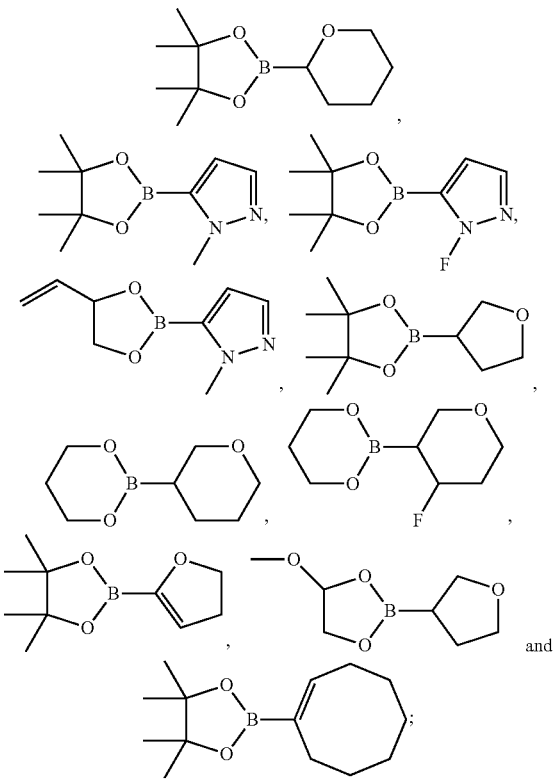

a content of the at least one compound accounts for b % of a weight of the electrolyte, wherein b % is 0.1% to 5%; and lithium difluorophosphate;

a content of the lithium difluorophosphate accounts for a % of the weight of the electrolyte;

wherein a range of a/b is 0.01-6.

* * * * *